US008440720B2

(12) United States Patent
Wang et al.

(10) Patent No.: US 8,440,720 B2
(45) Date of Patent: May 14, 2013

(54) METHODS OF USE OF ANTIVIRAL COMPOUNDS

(75) Inventors: Jizhou Wang, Eagleville, PA (US); Xiaodong Fan, Center Valley, PA (US); Lidia Cristian, Princeton Junction, NJ (US)

(73) Assignee: Influmedix, Inc., Radnor, PA (US)

( * ) Notice: Subject to any disclaimer, the term of this patent is extended or adjusted under 35 U.S.C. 154(b) by 212 days.

(21) Appl. No.: 12/881,038

(22) Filed: Sep. 13, 2010

(65) Prior Publication Data

US 2011/0065766 A1 Mar. 17, 2011

Related U.S. Application Data

(60) Provisional application No. 61/241,643, filed on Sep. 11, 2009.

(51) Int. Cl.
*A61K 31/185* (2006.01)
*A61K 31/13* (2006.01)
*A61K 31/16* (2006.01)
*A61K 31/015* (2006.01)

(52) U.S. Cl.
USPC .......................................... 514/579; 514/763

(58) Field of Classification Search .................. 514/579, 514/763
See application file for complete search history.

(56) References Cited

U.S. PATENT DOCUMENTS

| | | | |
|---|---|---|---|
| 3,328,251 A | 6/1967 | Smith | |
| 3,567,829 A | 3/1971 | Gagneux | |
| 4,005,224 A | 1/1977 | Tankersley | |
| 6,117,880 A | 9/2000 | Guo et al. | |
| 7,145,037 B2 | 12/2006 | Makovec et al. | |
| 7,951,816 B2 | 5/2011 | Kokubo et al. | |
| 2008/0108050 A1 | 5/2008 | Montelione et al. | |
| 2008/0293685 A1 | 11/2008 | Kong et al. | |
| 2010/0063080 A1 | 3/2010 | Press et al. | |
| 2010/0069420 A1 | 3/2010 | Degrado et al. | |
| 2011/0065766 A1 | 3/2011 | Wang et al. | |
| 2011/0236881 A1 | 9/2011 | Degrado et al. | |
| 2011/0288111 A1 | 11/2011 | Degrado et al. | |
| 2011/0294785 A1 | 12/2011 | Degrado et al. | |

FOREIGN PATENT DOCUMENTS

| | | |
|---|---|---|
| WO | WO 99/22735 | 5/1999 |
| WO | WO 2006/022454 | 3/2006 |
| WO | WO 2007/136737 | 11/2007 |
| WO | WO 2010/019712 | 2/2010 |
| WO | WO 2010/033339 | 3/2010 |
| WO | WO 2010/033340 | 3/2010 |
| WO | WO 2011/022191 | 2/2011 |

OTHER PUBLICATIONS

Adcock W, Trout NA. Transmission of Polar Substituent Effects in the Adamantane Ring System as Monitored by 19F NMR. Magn Reson Chem. Mar. 1998, 36(4); 181-195.*

Kolocouris A, Hansen RK, Broadhurst RW. Interaction between an amantadine analogue and the transmembrane portion of the influenza A M2 protein in liposomes probed by 1H NMR spectroscopy of the ligand. J Med Chem. Sep. 23, 2004;47(20):4975-8.*

Fischer W, Grob CA, Katayama H. 204. Die Synthese von 1,3-disubstituierten Adamantanen. Helv Chim Acta. Sep. 29, 1976;59(6):1953-62.*

Abdel-Magid et al., "Reductive Amination of Aldehydes and Ketones with Sodium Triacetoxyborohydride. Studies on Direct and Indirect Reductive Amination Procedures", J. Org. Chem., May 31, 1996, 61(11), 3849-3862.

Acharya, et al., "Influenza A Virus Employs Water Clusters to Sequester Charge in a Biological Membrane", Submitted to Science on Jun. 9, 2009, 1-41.

Balannik, et al., "Design and pharmacological characterization of inhibitors of amantadine-resistant mutants of the M2 ion channel of influenza A virus", Biochemistry, Dec. 22, 2009, 48(50), 11872-11882.

Betakova et al., "Influence of residue 44 on the activity of the M2 proton channel of influenza A virus", J. Gen. Virology, Jan. 2005, 86(Part 1), 181-184.

Braslau, et al., "The Synthesis and Evaluation of New α-Hydrogen Nitroxides for 'Living' Free Radical Polymerization", Synthesis-Stuttgart, Jun. 2005, 2005(9), 1496-1506.

Bright et al., "Adamantane resistance among influenza A viruses isolated early during the 2005-2006 influenza season in the United States", J. Am. Med. Assoc., Feb. 22, 2006, 295(8), 891-894.

Bright et al., "Incidence of adamantane resistance among influenza A (H3N2) viruses isolated worldwide from 1994 to 2005: a cause for concern", Lancet, Oct. 2005, 366(9492), 1175-1181.

Chang et al., "Membrane permeabilization by small hydrophobic nonstructural proteins of Japanese Encephalitis virus", J. of Virology, Aug. 1999, 73(8), 6257-6264.

Deyde et al., "Surveillance of resistance to adamantanes among influenza A(H3N2) and A(H1N1) viruses isolated worldwide", J. Infect. Dis., Jul. 15, 2007: Epub Jun. 7, 2007, 196(2), 249-257.

Ettmayer, et al., "Lessons learned from marketed and investigational prodrugs", Journal of Medicinal Chemistry, May 6, 2004, 47(10), 2394-2404.

Flaugh et al., "Acid-catalyzed annelation of α-alkylaldehydes and α,β-unsaturated ketones. A one-pot synthesis of 4,4-dimethyl-2-cyclohexen-1-one", J. Org. Chem., Dec. 1980, 45(26), 5399-5400.

Geluk, et al., "Hydride transfer reactions of the adamantyl cation (IV): Synthesis of 1,4- and 2,6-substituted adamantanes by oxidation with sulfuric acid", Recueil des Travaux Chimiques des Pays-Bas, 1971, 90(5), 516-520.

(Continued)

Primary Examiner — Paul Zarek
(74) Attorney, Agent, or Firm — Woodcock Washburn, LLP

(57) ABSTRACT

The present invention relates, in part, to methods of treatment, prevention, and inhibition of viral disorders. In one aspect, the present invention relates to inhibition of the M2 proton channel of influenza viruses (e.g. influenza A virus) and other similar viroporins (e.g., VP24 of Ebola and Marburg viruses; and NS3 protein of Bluetongue). The present invention further relates, inter alia, to compounds which have been shown to possess antiviral activity, in particular, inhibiting the M2 proton channel of influenza viruses.

26 Claims, No Drawings

OTHER PUBLICATIONS

GenBank Accession No. AAO46668, "Membrane ion channel M2 [Influenza A virus (A/Hong Kong/16/1968(H3N2))]", http://www.ncbi.nlm.nih.gov/protein/37933009?report=gpwithparts&log$= seqview#sequence37933009>, May 31, 2005, 4 pages (See Sequence on p. 3)

Gonzalez et al., "Viroporins", FEBS Letters, Sep. 18, 2003, 552(1), 28-34.

Grambas et al., "Influence of amantadine resistance mutations on the pH regulatory function of the M2 protein of influenza A viruses", Virology, Dec. 1992, 191(2), 541-549.

Greene et al., "Protective Groups in Organic Synthesis", Wiley & Sons $2^{nd}$ edition, 1991, 1-405.

Han et al., "Biochemical and functional characterization of the Ebola virus VP24 protein: Implications for a role in virus assembly and budding", J. of Virology, Feb. 2003, 77(3), 1793-1800.

Han et al., "The NS3 protein of Bluetongue virus exhibits viroporin-like properties", J.of Biol. Chem., Oct. 8, 2004, 279(41), 43092-43097.

Hayden, et al., "Plaque inhibition assay for drug susceptibility testing on Influenza viruses", Antimicrobial Agents and Chemotherapy, May 1980, 17(5), 865-870.

Hayden, F.G., "Antiviral resistance in Influenza viruses—Implications for management and pandemic response", N. Eng, J. Med., Feb. 23, 2006, 354(8), 785-788.

Higuchi et al., "Pro-drugs as novel drug delivery systems", A.C.S. Symposium Series, vol. 14, Jun. 1, 1975, 1-115.

Hu, et al., "Backbone Structure of the Amantadine-Blocked Trans-Membrane Domain M2 Proton Channel from Influenza A Virus", Biophysical Journal, Jun. 15, 2007, 92(12), 4335-4343.

Ito et al., "Evolutionary analysis of the influenza A virus M gene with comparison of the M1 and M2 proteins", J. of Virology, Oct. 1991, 65(10), 5491-5498.

Jefferson et al., "Antivirals for influenza in healthy adults: systematic review", Lancet, Jan. 2006, 367(9507), 303-313.

Jing et al., "Functional studies indicate amantadine binds to the pore of the influenza A virus M2 proton-selective ion channel", PNAS USA, Aug. 5, 2008, 105(31), 10967-10972.

Kalir, et al., "2-phenyl-2-adamantanamine hydrochloride— [Tricyclo[3.3.1.13,7]decan-2-amine, 2-phenyl, hydrochloride]", Organic Syntheses, 1981, 60, 104-108.

Khan et al., "Biological and Chemical Terrorism: Strategic Plan for Preparedness and Response", Recommendations of the CDC Strategic Planning Group, MMWR, Apr. 21, 2000, 49(RR-4), 1-14.

Kiso et al., "Resistant influenza A viruses in children treated with oseltamivir: descriptive study", Lancet, Aug.-Sep. 2004, 364(9436), 759-765.

Kolocouris et al., "Design and synthesis of bioactive adamantane spiro heterocycles", Bioorganic & Med. Chem. Lett., Aug. 2007, 17(15), 4358-4362.

Kurtz et al., "Growth impairment resulting from expression of influenza virus M2 protein in *Saccharomyces cerevisiae*: identification of a novel inhibitor of influenza virus", Antimicrob. Agents Chemotherapy., Oct. 1995, 39(10), 2204-2209.

Lamb et al., "The influenza A virus M2 ion channel protein and its role in the influenza virus life cycle", E. Wimmer ed., Receptor-Mediated Virus entry into Cells, Cold Spring Harbor Press, N.Y., 1994, 65-93 (Chapter 3).

Ma, et al., "Identification of the functional core of the influenza A virus A/M2 proton-selective ion channel", PNAS, Jul. 28, 2009, 106(30), 12283-12288.

Majerski, et al., "Rearrangement of bridgehead alcohols to polycyclic ketones by fragmentation-cyclization: 4-protoadamantanone (tricyclo-[4.3.1.03,8]decan-4-one)", Organic Syntheses, 1979, 59, 147-152.

Morissette, et al., "High-throughput crystallization: polymorphs, salts, co-crystals and solvates of pharmaceutical solids", Advanced Drug Delivery Reviews, Feb. 2004, 56(3), 275-300.

Moss, et al., "Conversion of 'obstinate' nitriles to amidines by Garigipati's reaction", Tetrahedron Letters, Nov. 27, 1995, 36(48), 8761-8764.

Nasr, et al., "Rigid Multivalent Scaffolds Based on Adamantane", J. Organic Chemistry, Feb. 1, 2008, 73(3), 1056-1060.

Okada, et al., "Protonation of Histidine and Histidine-Tryptophan Interaction in the Activation of the M2 Ion Channel from Influenza A Virus", Biochemistry, May 22, 2001, 40(20), 6053-6060.

Palandoken, et al., "A facile synthesis of (tert-alkoxy)amines", Tetrahedron Letters, Sep. 26, 2005, 46(39), 6667-6669.

Pinto, et al., "A functionally defined model for the M2 proton channel of influenza A virus suggests a mechanism for its ion selectivity", PNAS, Oct. 14, 1997, 94(21), 11301-11306.

Ramaiah, et al., "1-Trifluoromethyl-1-Cyclohexanol— [Cyclohexanol, 1-(trifluoromethyl)-]", Organic Syntheses, 1995, 72, 232-240.

Remington's Pharmaceutical Sciences, $17^{th}$ edition, Mack Publishing Company, Easton, PA, 1985, 1418-1419.

Rohde et al., "Discovery and metabolic stabilization of potent and selective 2-amino-N-(adamant-2-yl) acetamide 11 beta-hydroxysteroid dehydrogenase type 1 inhibitors", Journal of Med. Chem., Jan. 2007, 50(1), 149-164.

Schnell et sl., "Structure and mechanism of the M2 proton channel of influenza A virus", Nature, Jan. 31, 2008, 451(7178), 591-595.

Schulz et al., "SSM-based electrophysiology", Methods, Oct. 2008, 46(2), 97-103.

Shimbo, et al., "Ion selectivity and activation of the M2 ion channel of influenza virus", Biophysical Journal, Mar. 1996, 70(3), 1335-1346.

Stella, Valentino J., "Prodrugs as therapeutics", Expert Opinion on Therapeutic Patents, Mar. 2004, 14(3), 277-280.

Stouffer, et al., "Structural basis for the function and inhibition of an influenza virus proton channel", Nature, Jan. 31, 2008, 451(7178), 596-599.

Stouffer, et al., "Structural basis for the function and inhibition of an influenza virus proton channel", Nature Corrigendum, Mar. 20, 2008, 452(7185), 380.

Testa, Bernard, "Prodrug research: futile or fertile?", Biochemical Pharmacology, Dec. 2004, 68(11), 2097-2106.

Tian, et al., "Initial structural and dynamic characterization of the M2 protein transmembrane and amphipathic helices in lipid bilayers", Protein Science, Nov. 2003, 12(11), 2597-2605.

Tu et al., "Characterization of inhibition of M2 ion channel activity by BL-1743, an inhibitor of influenza A virus", J. Virol., Jul. 1996, 70(7), 4246-4252.

Turner et al., "A facile route to imidazol-4-yl anions and their reaction with carbonyl compounds", J. Org. Chem., Sep. 1991, 56(20), 5739-5740.

Van Niekerk et al., "Membrane Association of African Horsesickness Virus Nonstructural Protein NS3 Determines Its Cytotoxicity", Virology, Jan. 2001, 279(2), 499-508.

Venkataraman et al., "Chemical rescue of histidine selectivity filter mutants of the M2 ion channel of influenza A virus", J. Biol. Chem., Jun. 3, 2005, 280(22), 21463-21472.

Vippagunta, et al., "Crystalline solids", Adv. Drug Delivery Reviews, May 2001, 48(1), 3-26.

Wang et al., "Discovery of spiro-piperidine inhibitors and their modulation of the dynamics of the M2 proton channel from influenza A virus", J. Am. Chem. Soc., Jun. 17, 2009; Epub Mar. 26, 2009, 131(23), 8066-8076.

Wareing, et al., "CXCR2 is required for neutrophil recruitment to the lung during influenza virus infection, but is not essential for viral clearance", Viral Immunology, Sep. 2007, 20(3), 369-377.

Winum et al, "N-(tert-butoxycarbonyl)-N-[4-(dimethylazaniumylidene)-1,4-dihydropyridin-1-ylsulfonyl]azanide: a new sulfamyolating agent. Structure and reactivity toward amines", Org. letters, Jul. 12, 2001, 3(14), 2241-2243.

Wolff, et al., "Metabolic Considerations in Prodrug Design", Burger's Medicinal Chemistry and Drug Discovery, John Wiley & Sons, $5^{th}$ edition, vol. 1: Principles and Practice, Feb. 1995, 975-977.

Yi et al., "A secondary gate as a mechanism for inhibition of the M2 proton channel by amantadine", J. Phys. Chem. B., Jul. 10, 2008; E pub May 14, 2008, 112(27), 7977-7799.

\* cited by examiner

METHODS OF USE OF ANTIVIRAL COMPOUNDS

CROSS-REFERENCE TO RELATED APPLICATION

The present application claims priority to U.S. Provisional Application No. 61/241,643, filed Sep. 11, 2009, which is hereby incorporated by reference in its entirety.

TECHNICAL FIELD

The present invention relates, in part, to methods of treatment, prevention, and inhibition of viral disorders. In one aspect, the present invention relates to inhibition of the M2 proton channel of influenza viruses (e.g., influenza A virus and/or influenza B virus) and other similar viroporins (e.g., VP24 of Ebola and Marburg viruses; and NS3 protein of Bluetongue). The present invention further relates to compounds which have been shown to possess antiviral activity, in particular, inhibiting the M2 proton channel (e.g., wild type and/or drug resistant influenza such as S31N influenza or other drug-resistant influenza strains) of influenza viruses and other similar viroporins.

BACKGROUND

Viroporins are a growing class of membrane proteins that are important for viral replication and packaging. These proteins also affect cellular functions, including the cell vesicle system, glycoprotein trafficking and membrane permeability (Gonzalez et al., FEBS Lett., 2003, 552, 28-34). The M2 proton channel is a prototype for this class of proteins that is essential to the survival of the virus (Lamb et al., Wimmer E, editor, Receptor-Mediated Virus Entry into Cells, Cold Spring Harbor, N.Y., Cold Spring Harbor Press, 1994, p. 303-321).

Viroporins are essential components of a variety of viruses including Ebola, Marburg, Bluetongue, African horse sickness, foot and mouth disease, and Japanese encephalitis viruses. In particular, Ebola and Marburg viruses pose a particularly serious threat to human health and are classified as category A biowarfare agents by the Center for Disease Control (CDC) (Khan et al., MMWR, 2000, 49, RR-4, 1-14. VP24 from Ebola and Marburg viruses is an integral membrane protein that possesses viroporin activity similar to the M2 protein (Han et al., J. Virology, 2003, 77(3), 793-800). NS3 protein of Bluetongue is a viroporin that is critical for virus release (Han et al., J. Biol. Chem., 2004, 279, 41, 43092-43097). In addition, picronaviruses (Gonzalez et al., FEBS Lett., 2003, 552, 28-34), African horse sickness, and Japanese encephalitis encode proteins with viroporin activity that play central roles in viral pathogenesis (Van Niekerk et al., Virology, 2001, 279, 499-508; Chang et al., J. Virol., 1999, 73(8), 6257-6264).

Influenza viruses infect the upper and lower respiratory tracts and cause substantial morbidity and mortality annually. Influenza A viruses, which also infect a wide number of avian and mammalian species, pose a considerable public health burden with epidemic and pandemic potential. Influenza together with complications of the virus is consistently among the top 10 common causes of death, ranking higher than some other much more widely publicized killers, such as the HIV virus that causes AIDS. It is estimated that in annual influenza epidemics, 5-15% of the world's population contracts influenza, resulting in an estimated 3-5 million cases of severe illness and 250,000 to 500,000 deaths around the world from influenza-associated complications. In the U.S., 10%-20% of the population is infected with the flu every year, with an average 0.1% mortality. The flu causes 36,000 deaths each year in the U.S., and 114,000 hospitalizations. The cost of influenza epidemics to the U.S. economy is estimated at $3-15 billion. Approximately 20% to 40% of the world's population became ill during the catastrophic "Spanish" flu pandemic in 1918, which killed an estimated 40 to 50 million people worldwide and 675,000 people in the United States. The "Asian" flu pandemic of 1957 resulted in the deaths of approximately 69,800 people in the United States and 2.0 to 7.4 million worldwide. The H1N1 swine flu pandemic in 2009 has caused about 3,000 deaths worldwide to date.

Tamiflu (oseltamivir), which targets neuraminidase protein, is the only remaining orally administered anti-flu drug on the market and resistance to the drug is increasing with oseltamivir-resistant viruses arising during clinical use of the drug in children (Kiso et al., Lancet, 2004, 364, 759-65). Oseltamivir has been used for treatment of infected individuals and although it is FDA-approved for prophylaxis its usefulness for prophylactic treatment has been questioned in a recent systematic analysis of data from 51 controlled trials (Jefferson et al., Lancet, 2006, 367, 303-13). Thus, there is an immediate need to develop additional agents that inhibit the M2 proton channel and its drug-resistant forms, and in particular the most prevalent mutant form, S31N, but also in others including L26, V27, A30, and G34.

Influenza A and B viruses each encode a small oligomeric integral membrane protein, M2 of influenza A virus and BM2 of influenza B virus, each of which is a proton-selective ion channel. The M2 protein plays an important role during the early and late stages of the viral life cycle. Early in the cycle, the virus enters cells by receptor-mediated endocytosis, which places the virus into endosomal vesicles. Proton-pumping ATP-ases in the endosomal membrane lower the internal pH, which triggers the fusion of the viral envelope with the endosomal membrane and the release of the viral RNA into the cytoplasm. However, unless the inside of the virus is acidified prior to fusion, the RNA remains encapsulated by a matrix protein known as M1 (Ito et al., J. Virol., 1981, 65, 5491-8). The M2 protein provides a conduit for passage of protons into the interior of the virus, thereby promoting the dissociation of RNA from its matrix protein. This is a crucial step in uncoating of the virus and exposing its content to the cytoplasm of the host cell. In some strains of influenza A virus, the M2 protein is also important for equilibrating the pH of the lumen of the Golgi apparatus with the cytoplasm, thus preventing a premature conformational change in the viral hemagglutinin at the wrong time and in the wrong place (Ciampor et al., Acta Virologica, 1995, 39, 171-181). Inhibition of M2 at this later stage of the viral life cycle prevents viral maturation and release from the host cell.

Several features make M2 an excellent target for an anti-influenza drug. It is essential and present in all known isolates of influenza A virus, and it is already validated as a drug target. Although a variety of mutations occur naturally and can be isolated in cell culture, one mutant in particular, S31N, predominates in more than 98% of the transmissible resistant viral strains isolated from patients in the last decade (Bright et al., Lancet, 2005, 366, 1175-1181).

Thus, there is a great need for additional compositions and methods of treatment based on the use of antiviral compounds against key viral pathogens and, optionally, less prone to the development of resistance by those pathogens. Moreover, there is a great need for additional compositions and methods of treatment based on the use of antiviral compounds that are effective in the treatment of viral pathogens that have already developed resistance to existing antiviral agents. In particular, there is a great need for effective compositions and methods for the treatment of viral infections such as influenza, Ebola, Marburg, bluetongue, foot and mouth disease, African horse sickness, and Japanese encephalitis (including the strains that have already developed resistance to existing antiviral agents). The present invention is directed to these and other important ends.

SUMMARY

The present invention provides, in part, methods for treating an influenza virus-affected disease state or infection comprising the step of administering to a subject in need thereof a composition comprising a compound of Formula I:

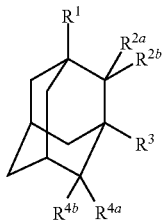

or a pharmaceutically acceptable salt thereof, wherein $R^1$, $R^{2a}$, $R^{2b}$, $R^3$, $R^{4a}$, and $R^{4b}$ are as defined herein.

In some embodiments, the present invention provides methods for treating a viral infection, such as influenza (e.g., wild-type influenza, such as wild-type influenza A or B, or one or more mutant varieties of influenza such as S31N influenza), Ebola, Marburg, bluetongue, foot and mouth disease, African horse sickness, and Japanese encephalitis, in a patient (including a human or an animal) comprising administering to a subject in need thereof a composition comprising a compound of Formula I as defined herein.

Also provided are compositions comprising a compound according to Formula I or a pharmaceutically acceptable salt or stereoisomer thereof, and a pharmaceutically acceptable carrier, diluent, or excipient.

Also disclosed are compounds according to Formula II

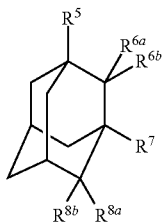

or a pharmaceutically acceptable salt thereof, wherein $R^5$, $R^{6a}$, $R^{6b}$, $R^7$, $R^{8a}$, and $R^{8b}$ are as defined herein, and compositions comprising one or more of such compounds or salts thereof, that can be administered for the treatment or prevention of a viral infection such as influenza (e.g., wild type influenza or drug resistant influenza such as S31N influenza), Ebola, Marburg, bluetongue, foot and mouth disease, African horse sickness, and Japanese encephalitis in patients (including humans or other animals).

DETAILED DESCRIPTION

The present invention may be understood more readily by reference to the following detailed description taken in connection with the accompanying figures and examples, which form a part of this disclosure. It is to be understood that this invention is not limited to the specific products, methods, conditions or parameters described and/or shown herein, and that the terminology used herein is for the purpose of describing particular embodiments by way of example only and is not intended to be limiting of the claimed invention.

The disclosures of each patent, patent application, and publication cited or described in this document are hereby incorporated herein by reference, in their entirety.

As employed above and throughout the disclosure, the following terms and abbreviations, unless otherwise indicated, shall be understood to have the following meanings.

In the present disclosure the singular forms "a," "an," and "the" include the plural reference, and reference to a particular numerical value includes at least that particular value, unless the context clearly indicates otherwise. Thus, for example, a reference to "a compound" is a reference to one or more of such compounds and equivalents thereof known to those skilled in the art, and so forth. Furthermore, when indicating that a certain chemical moiety "may be" X, Y, or Z, it is not intended by such usage to exclude in all instances other choices for the moiety; for example, a statement to the effect that $R_1$ "may be alkyl, aryl, or amino" does not necessarily exclude other choices for $R_1$, such as halo, aralkyl, and the like.

When values are expressed as approximations, by use of the antecedent "about," it will be understood that the particular value forms another embodiment. As used herein, "about X" (where X is a numerical value) preferably refers to ±10% of the recited value, inclusive. For example, the phrase "about 8" refers to a value of 7.2 to 8.8, inclusive; as another example, the phrase "about 8%" refers to a value of 7.2% to 8.8%, inclusive. Where present, all ranges are inclusive and combinable. For example, when a range of "1 to 5" is recited, the recited range should be construed as including ranges "1 to 4", "1 to 3", "1-2", "1-2 & 4-5", "1-3 & 5", and the like. In addition, when a list of alternatives is positively provided, such listing can be interpreted to mean that any of the alternatives may be excluded, e.g., by a negative limitation in the claims. For example, when a range of "1 to 5" is recited, the recited range may be construed as including situations whereby any of 1, 2, 3, 4, or 5 are negatively excluded; thus, a recitation of "1 to 5" may be construed as "1 and 3-5, but not 2", or simply "wherein 2 is not included." In another example, when a listing of possible substituents including "hydrogen, alkyl, and aryl" is provided, the recited listing may be construed as including situations whereby any of "hydrogen, alkyl, and aryl" is negatively excluded; thus, a recitation of "hydrogen, alkyl, and aryl" may be construed as "hydrogen and aryl, but not alkyl", or simply "wherein the substituent is not alkyl".

It has presently been discovered that certain adamantane variants are effective for inhibiting the respective viroporins of various virus species, including virus species in which a mutation of the viroporin and/or associated structures is present. Some of the adamantane variants concerning which this discovery has been made are commercially available, and others have been newly conceived by the present inventors. As used herein, "inhibition" of a viroporin refers to the reduction of the viroporin's ability to function in a manner that is most consistent with the vitality of the virus of which the viroporin is a component.

Accordingly, in one aspect, the present invention provides methods for treating an influenza virus-affected disease state or infection comprising the step of administering to a subject in need thereof a composition comprising a compound of Formula I:

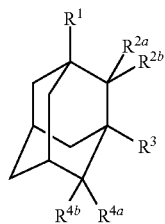

or a pharmaceutically acceptable salt thereof, wherein:

$R^1$ is amino, amino($C_1$-$C_3$)alkyl, nitro, nitro($C_1$-$C_3$)alkyl, formamidinyl, guanidinyl, —CH(OH)CH$_2$NO$_2$, ($C_1$-$C_3$)alkylamino, a five- or six-membered heterocyclic ring, or together with $R^{2a}$ or $R^{2b}$ forms a five- or six-membered optionally substituted carbocyclic or heterocyclic ring;

$R^{2a}$ and $R^{2b}$ are independently hydrogen, hydroxyl, ($C_1$-$C_3$)alkyl optionally substituted with halo, ($C_1$-$C_3$)alkoxy, halo, or together with $R^1$ forms a five- or six-membered carbocyclic or heterocyclic ring;

$R^3$ is hydrogen, halo, hydroxyl, ($C_1$-$C_3$)alkoxy, thiol, or thio($C_1$-$C_3$)alkyl; and, $R^{4a}$ and $R^{4b}$ are independently hydrogen, hydroxyl, halo, thiol, thionyl, cyano, ($C_1$-$C_3$)alkyl optionally substituted with halo, ($C_1$-$C_3$)alkoxy, oxo, oxime, hydroxy($C_1$-$C_3$)alkyl, or $R^{4a}$ and $R^{4b}$ together with the carbon atom to which they are both attached form a three- to six-membered carbocyclic or heterocyclic ring, wherein:

at least one of $R^{2a}$ or $R^{2b}$; $R^3$; or $R^{4a}$ and $R^{4b}$ are other than hydrogen, or, $R^1$ includes or is involved in forming a five- or six-membered heterocyclic or carbocyclic ring that is directly bound to the carbon atom to which $R^1$ is attached.

In some embodiments, $R^1$ is a substituted or unsubstituted imidazole, pyrazole, pyrrolidine, or triazole ring. Such rings may be saturated, partially unsaturated, or fully unsaturated. For example, the $R^1$ may be a 4,5-dihydro-1H-imidazole ring. Substituents on the ring forming $R^1$ may include, for example, amino or oxo. When $R^1$ is a substituted or unsubstituted imidazole, pyrazole, pyrrolidine, or triazole ring, $R^{2a}$, $R^{2b}$, $R^3$, $R^{4a}$, and $R^{4b}$ may all be hydrogen.

With respect to other embodiments, $R^1$ may be amino($C_1$-$C_3$)alkyl. When $R^1$ is amino($C_1$-$C_3$)alkyl, $R^{4a}$ and $R^{4b}$ may independently be, for example, hydrogen, halo, hydroxyl, ($C_1$-$C_3$)alkyl, or ($C_1$-$C_3$)alkoxy. In one embodiment, $R^1$ is amino($C_2$)alkyl, wherein alkyl is substituted with hydroxyl.

In other instances, $R^1$ may be amino. When $R^1$ is amino, $R^{4a}$ and $R^{4b}$ may independently be, for example, hydrogen, halo, hydroxyl, oxo, cyano, ($C_1$-$C_3$)alkyl optionally substituted with halo, thionyl, thiol, or oxime, or, $R^{4a}$ and $R^{4b}$ together with the carbon atom to which they are both attached form a three- to six-membered carbocyclic or heterocyclic ring. When $R^1$ is amino, and $R^{4a}$ and $R^{4b}$ are independently selected from the preceding list, there are certain embodiments in which $R^{2a}$, $R^{2b}$, and $R^3$ are hydrogen. In other embodiments wherein $R^1$ is amino, $R^{4a}$ and $R^{4b}$ together with the carbon atom to which they are both attached form a three- to six-membered carbocyclic or heterocyclic ring. For example, $R^{4a}$ and $R^{4b}$ together with the carbon atom to which they are both attached may form a five-membered carbocyclic or heterocyclic ring, and wherein the ring is heterocyclic, it may include one or two heteroatoms, such as nitrogen, oxygen, or both. In other instances wherein $R^1$ is amino, $R^3$ may be hydrogen, halo, or ($C_1$-$C_3$)alkoxy.

With respect to still other embodiments, $R^1$ may be nitro or nitro($C_1$-$C_3$)alkyl. When $R^1$ is selected thusly, $R^{4a}$ and $R^{4b}$ may independently be, for example, hydrogen, ($C_1$-$C_3$)alkoxy, hydroxyl, or halo. For example, one of $R^{4a}$ and $R^{4b}$ may be hydrogen, and the other of $R^{4a}$ and $R^{4b}$ may be methoxy, hydroxyl, or fluoro.

$R^1$ may also be chosen such that that substituent together with $R^{2a}$ or $R^{2b}$ forms a five- or six-membered optionally substituted carbocyclic or heterocyclic ring. For example, $R^1$ may together with $R^{2a}$ or $R^{2b}$ form a five-membered heterocyclic ring that bears nitrogen, oxygen, or both nitrogen and oxygen heteroatoms.

Exemplary compounds according to formula I that may be used pursuant to the present methods include:

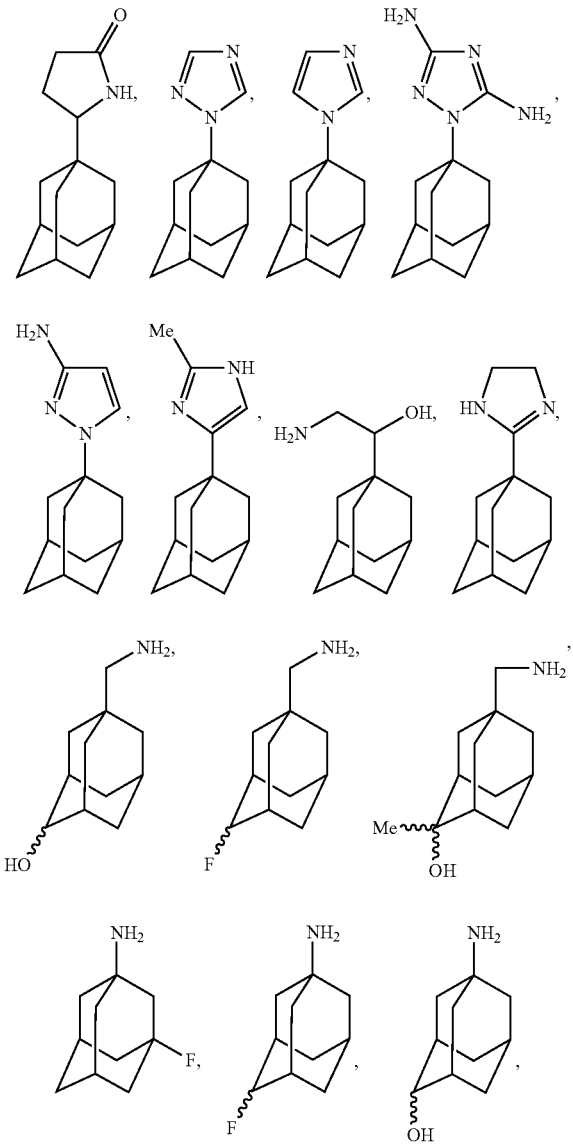

or a pharmaceutically acceptable salt or stereoisomer thereof.

In some embodiments, the methods provided herein inhibit an M2 proton channel (i.e., M2 protein or M2) of an influenza virus (including M2 of an influenza A virus and/or BM2 of an influenza B virus). In some embodiments, the M2 belongs to a wild type influenza virus. In some embodiments, the M2 belongs to an influenza virus strain that is resistant to the existing anti-influenza drugs (such as amantadine and/or rimantadine), for example, a S31N mutant. The mutant virus may comprise an influenza virus having the L26F mutation; may comprise an influenza virus having the V27G mutation, the V27I mutation, the V27T mutation, the V27S mutation, or the V27A mutation; may comprise an influenza virus having the A30T mutation; may comprise an influenza virus having the S31A mutation or the S31N mutation; may an influenza virus having the G34E mutation or the G34A mutation; may comprise an influenza virus having the L38F mutation; may comprise an influenza virus having the W41L mutation or the W41Y mutation; may comprise an influenza virus having the D44N mutation or the D44H mutation; and/or may comprise an influenza virus having the R45K mutation or the R45H mutation.

In some embodiments, the methods provided herein inhibit VP24 of an Ebola or a Marburg virus.

In some embodiments, the methods provided herein inhibit NS3 protein of a Bluetongue virus.

In some embodiments, the methods provided herein inhibit a viroporin of a picornavirus, foot and mouth disease virus, African horse sickness virus, or Japanese encephalitis virus.

In some embodiments, the compounds and/or salts provided herein can inhibit (i.e., decrease activity of) an M2 proton channel of an influenza virus (including M2 of an influenza A virus; BM2 of an influenza B virus, M2 of a wild type influenza virus, and/or M2 of a drug resistant influenza such as S31N influenza or other drug-resistant strains) by, for example, binding to the transmembrane region of M2 and interfering with proton conduction inside the virus and ultimately preventing the replication of the virus. In some embodiments, the compounds and/or salts provided herein can inhibit M2 and prevent viral maturation and release from the host cell. Accordingly, in some embodiments, the present invention provides a method for treating influenza (including wild type influenza and/or drug resistant influenza such as S31N influenza or other drug-resistant strains) in a patient (including a human or another animal) comprising contacting the patient with a therapeutically effective amount of a compound of Formula I as defined herein. In some embodiments, the method is a method for treating influenza that is a wild type. In some embodiments, the method is for treating influenza that is resistant to one or more of the existing anti-influenza drugs. In some embodiments, the method is a method for treating influenza that is resistant to amantadine and/or rimantadine.

In some embodiments, the compounds and/or salts provided herein can inhibit other integral membrane proteins that possess viroporin activity similar to the M2 protein (for example, VP24 of Ebola and Marburg viruses, NS3 protein of a Bluetongue virus, and a viroporin of a picornavirus, foot and mouth disease virus, African horse sickness virus, or Japanese encephalitis virus). Accordingly, in some embodiments, the present invention provides methods for treating Ebola, Marburg, bluetongue, foot and mouth disease, African horse sickness, and Japanese encephalitis in a patient (including a human or another animal) comprising contacting the patient with a therapeutically effective amount of the compound of Formula I as defined herein. In some embodiments, the method is a method for treating Ebola or Marburg in a patient. In some embodiments, the method is a method for treating Bluetongue in a patient. In some embodiments, the method is a method of treating a picornavirus infection, foot and mouth disease, African horse sickness, or Japanese encephalitis in a patient.

Methods of measuring inhibition of M2 protein of an influenza virus (or other integral membrane proteins that possess viroporin activity similar to the M2 protein (for example, VP24 of Ebola and Marburg viruses, NS3 protein of a Bluetongue virus, and a viroporin of a picornavirus, foot and mouth disease, African horse sickness, or Japanese encephalitis virus) are routine in the art.

The present invention further provides methods for treating viral infections such as influenza, Ebola, Marburg, bluetongue, foot and mouth disease, African horse sickness, and Japanese encephalitis in an individual (e.g., patient) by administering to the individual in need of such treatment a therapeutically effective amount or dose of a compound of Formula I as defined herein or a pharmaceutical composition thereof.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal. In some embodiments, the cell is an adipocyte, a pancreatic cell, a hepatocyte, neuron, or cell of the eye.

As used herein, the term "contacting" refers to the bringing together of indicated moieties in an in vitro system or an in vivo system. For example, "contacting" the M2 protein (i.e., the M2 proton channel) of an influenza virus with a compound in the invention includes the administration of a compound in the present invention to an individual or patient, such as a human, having an influenza infection, as well as, for example, introducing a compound of the invention into a sample containing a cellular or purified preparation containing the M2 protein.

As used herein, the term "individual" or "patient," used interchangeably, refers to any animal, including mammals, such as mice, rats, other rodents, rabbits, dogs, cats, swine, cattle, sheep, horses, or primates, such as humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician, which includes one or more of the following:

(1) preventing the disease; for example, preventing a disease, condition or disorder in an individual who may be predisposed to the disease, condition or disorder but does not yet experience or display the pathology or symptomatology of the disease;

(2) inhibiting the disease; for example, inhibiting a disease, condition or disorder in an individual who is experiencing or displaying the pathology or symptomatology of the disease, condition or disorder (i.e., including arresting further development of the pathology and/or symptomatology); and (3) ameliorating the disease; for example, ameliorating a disease, condition or disorder in an individual who is experiencing or displaying the pathology or symptomatology of the disease, condition or disorder (i.e., including reversing the pathology and/or symptomatology).

A subject or patient in whom administration of the therapeutic compound is an effective therapeutic regimen for a disease or disorder is preferably a human, but can be any animal, including a laboratory animal in the context of a clinical trial or screening or activity experiment. Thus, as can be readily appreciated by one of ordinary skill in the art, the methods, compounds and compositions of the present invention are particularly suited to administration to any animal, particularly a mammal, and including, but by no means limited to, humans, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, and the like, avian species, such as chickens, turkeys, songbirds, and the like, i.e., for veterinary medical use.

In other aspects, provided are compositions comprising a compound according to Formula I as defined herein or a pharmaceutically acceptable salt or stereoisomer thereof and a pharmaceutically acceptable carrier, diluent, or excipient. The applicable carrier, diluent, or excipient may be selected on the basis of the chosen route of administration and standard pharmaceutical practice as described, for example, in *Remington's Pharmaceutical Sciences* (Mack Pub. Co., Easton, Pa., 1985), the disclosure of which is hereby incorporated by reference in its entirety.

With respect to certain embodiments, the present compositions may further comprise a therapeutically effective amount of a further agent that modulates, for example, an influenza virus, such as Influenza A virus, Influenza B virus, or another Viroporin-type virus. For example, the further agent that modulates virus may be a known anti-viral agents, such as Tamiflu®, Relenza®, or peramivir. In certain embodiments, the present compositions comprise a therapeutically effective amount of a compound of formula I which is administered in combination with immunizations or vaccines that are effective in preventing or lessening the symptoms of influenza. Examples include antibodies, immune suppressants, anti-inflammatory agents, and the like.

In another aspect of the present invention, provided are compounds of the formula II:

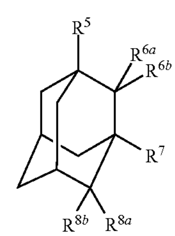

or a pharmaceutically acceptable salt thereof, wherein $R^5$ is amino, amino($C_1$-$C_3$)alkyl, nitro, nitro($C_1$-$C_3$)alkyl, guanidinyl, or together with $R^{6a}$ or $R^{6b}$ forms a five- or six-membered optionally substituted carbocyclic or heterocyclic ring;

$R^{6a}$ and $R^{6b}$ are independently hydrogen, hydroxyl, ($C_1$-$C_3$)alkyl optionally substituted with halo, or together with $R^1$ forms a five- or six-membered carbocyclic or heterocyclic ring;

$R^7$ is hydrogen, and, if $R^1$ is other than amino or halo; and, $R^{8a}$ and $R^{8b}$ are independently hydrogen, hydroxyl, halo, cyano, ($C_1$-$C_3$)alkyl optionally substituted with halo, ($C_1$-$C_3$) alkoxy, thiol, thionyl, oxime, or $R^{8a}$ and $R^{8b}$ together with the carbon atom to which they are both attached form a three- to six-membered carbocyclic or heterocyclic ring, wherein said compound is substituted at two or more positions, and wherein if $R^5$ includes an —$NH_2$ group, and one of $R^{6a}$ and $R^{6b}$, or one of $R^{8a}$ and $R^{8b}$ is hydroxyl, then the other of $R^{6a}$ and $R^{6b}$ or the other of $R^{8a}$ and $R^{8b}$ are not hydrogen.

In some embodiments, $R^5$ is amino($C_1$-$C_3$)alkyl. In such instances, $R^{8a}$ and $R^{8b}$ may independently be hydrogen, halo, hydroxyl, $(C_1-C_3)$alkyl, or $(C_1-C_3)$alkoxy. For example, $R^{8a}$ and $R^{8b}$ may independently be methoxy, fluoro, methyl, or hydroxyl.

$R^5$ may be amino. When $R^5$ is amino, $R^{8a}$ and $R^{8b}$ may independently be hydrogen, halo, hydroxyl, cyano, $(C_1-C_3)$ alkyl optionally substituted with halo, thionyl, thiol, oxime, or $R^{8a}$ and $R^{8b}$ together with the carbon atom to which they are both attached form a three- to six-membered carbocyclic or heterocyclic ring. When $R^5$ is amino, and $R^{8a}$ and $R^{8b}$ are independently selected from the preceding list, there are certain embodiments in which $R^{6a}$, $R^{6b}$, and $R^7$ are hydrogen. In other embodiments wherein $R^5$ is amino, $R^{8a}$ and $R^{8b}$ together with the carbon atom to which they are both attached form a three- to six-membered carbocyclic or heterocyclic ring. For example, $R^{8a}$ and $R^{8b}$ together with the carbon atom to which they are both attached may form a five-membered carbocyclic or heterocyclic ring, and wherein the ring is heterocyclic, it may include one or two heteroatoms, such as nitrogen, oxygen, or both. In other instances wherein $R^5$ is amino, $R^7$ may be hydrogen, halo, or $(C_1-C_3)$alkoxy.

With respect to still other embodiments, $R^5$ may be nitro or nitro$(C_1-C_3)$alkyl. When $R^5$ is selected thusly, $R^{8a}$ and $R^{8b}$ may independently be, for example, hydrogen, $(C_1-C_3)$ alkoxy, hydroxyl, or halo. For example, one of $R^{8a}$ and $R^{8b}$ may be hydrogen, and the other of $R^{8a}$ and $R^{8b}$ may be methoxy, hydroxyl, or fluoro.

In certain instances $R^5$ together with $R^{6a}$ or $R^{6b}$ may form a five- or six-membered optionally substituted carbocyclic or heterocyclic ring. For example, $R^5$ may together with $R^{6a}$ or $R^{6b}$ form a five-membered heterocyclic ring that bears nitrogen, oxygen, or both nitrogen and oxygen heteroatoms.

Exemplary compounds according to formula I that may be used pursuant to the present methods include:

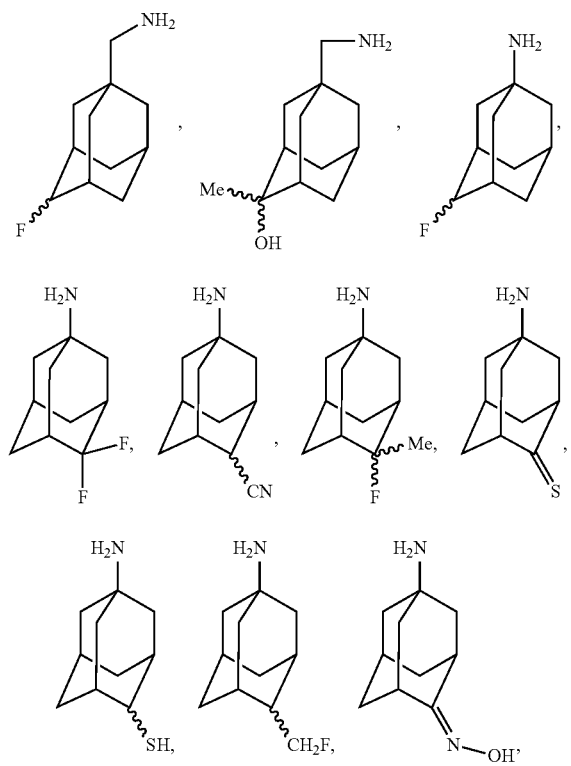

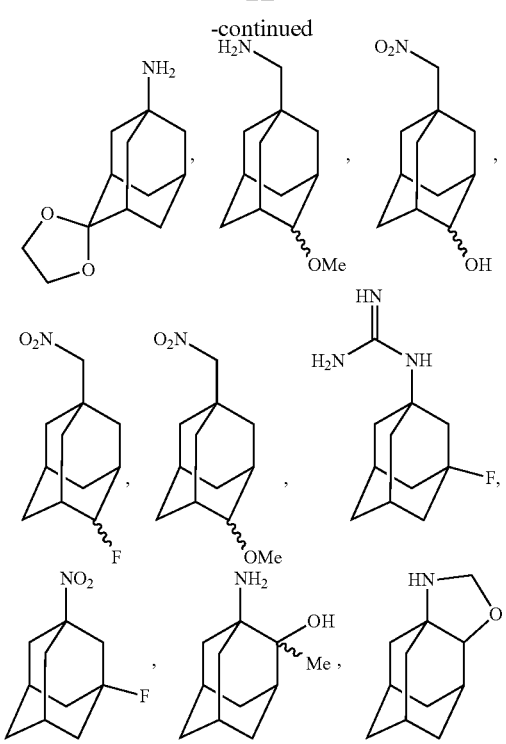

pharmaceutically acceptable salt or stereoisomer thereof.

The compounds of this invention may be administered orally or parenterally, neat or in combination with conventional pharmaceutical carriers, diluents, or excipients, which may be liquid or solid. The applicable solid carrier, diluent, or excipient may function as, among other things, a binder, disintegrant, filler, lubricant, glidant, compression aid, processing aid, color, sweetener, preservative, suspending/dispersing agent, tablet-disintegrating agent, encapsulating material, film former or coating, flavors, or printing ink. Of course, any material used in preparing any dosage unit form is preferably pharmaceutically pure and substantially non-toxic in the amounts employed. In addition, the active compound may be incorporated into sustained-release preparations and formulations. Parenteral administration in this respect includes administration by, inter alia, the following routes: intravenous, intramuscular, subcutaneous, intraocular, intrasynovial, transepithelial including transdermal, ophthalmic, sublingual and buccal; topically including ophthalmic, dermal, ocular, rectal and nasal inhalation via insufflation, aerosol, and rectal systemic.

In powders, the carrier, diluent, or excipient may be a finely divided solid that is in admixture with the finely divided active ingredient. In tablets, the active ingredient is mixed with a carrier, diluent or excipient having the necessary compression properties in suitable proportions and compacted in the shape and size desired. For oral therapeutic administration, the active compound may be incorporated with the carrier, diluent, or excipient and used in the form of ingestible tablets, buccal tablets, troches, capsules, elixirs, suspensions, syrups, wafers, and the like. The amount of active compound(s) in such therapeutically useful compositions is preferably such that a suitable dosage will be obtained. The therapeutic compositions preferably contain up to about 99% of the active ingredient.

Liquid carriers, diluents, or excipients may be used in preparing solutions, suspensions, emulsions, syrups, elixirs, and the like. The active ingredient of this invention can be dissolved or suspended in a pharmaceutically acceptable liquid such as water, an organic solvent, a mixture of both, or pharmaceutically acceptable oils or fat. The liquid carrier, excipient, or diluent can contain other suitable pharmaceutical additives such as solubilizers, emulsifiers, buffers, preservatives, sweeteners, flavoring agents, suspending agents, thickening agents, colors, viscosity regulators, stabilizers, or osmo-regulators.

Suitable solid carriers, diluents, and excipients may include, for example, calcium phosphate, silicon dioxide, magnesium stearate, talc, sugars, lactose, dextrin, starch, gelatin, cellulose, methyl cellulose, ethylcellulose, sodium carboxymethyl cellulose, microcrystalline cellulose, polyvinylpyrrolidine, low melting waxes, ion exchange resins, croscarmellose carbon, acacia, pregelatinized starch, crospovidone, HPMC, povidone, titanium dioxide, polycrystalline cellulose, aluminum methahydroxide, agar-agar, tragacanth, or mixtures thereof.

Suitable examples of liquid carriers, diluents and excipients for oral and parenteral administration include water (particularly containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil), or mixtures thereof.

For parenteral administration, the carrier, diluent, or excipient can also be an oily ester such as ethyl oleate and isopropyl myristate. Also contemplated are sterile liquid carriers, diluents, or excipients, which are used in sterile liquid form compositions for parenteral administration. Solutions of the active compounds as free bases or pharmacologically acceptable salts can be prepared in water suitably mixed with a surfactant, such as hydroxypropylcellulose. A dispersion can also be prepared in glycerol, liquid polyethylene glycols, and mixtures thereof and in oils. Under ordinary conditions of storage and use, these preparations may contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. In all cases, the form is preferably sterile and fluid to provide easy syringability. It is preferably stable under the conditions of manufacture and storage and is preferably preserved against the contaminating action of microorganisms such as bacteria and fungi. The carrier, diluent, or excipient may be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating, such as lecithin, by the maintenance of the required particle size in the case of a dispersion, and by the use of surfactants. The prevention of the action of microorganisms may be achieved by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions may be achieved by the use of agents delaying absorption, for example, aluminum monostearate and gelatin.

Sterile injectable solutions may be prepared by incorporating the active compounds in the required amounts, in the appropriate solvent, with various of the other ingredients enumerated above, as required, followed by filtered sterilization. Generally, dispersions may be prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation may include vacuum drying and the freeze drying technique that yields a powder of the active ingredient or ingredients, plus any additional desired ingredient from the previously sterile-filtered solution thereof.

The compounds of the invention may be administered in an effective amount by any of the conventional techniques well-established in the medical field. The compounds employed in the methods of the present invention including, for example, the compounds of formula I may be administered by any means that results in the contact of the active agents with the agents' site or sites of action in the body of a patient. The compounds may be administered by any conventional means available.

Preferably the pharmaceutical composition is in unit dosage form, e.g. as tablets, buccal tablets, troches, capsules, elixirs, powders, solutions, suspensions, emulsions, syrups, wafers, granules, suppositories, or the like. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form. In addition, dosage forms of the present invention can be in the form of capsules wherein one active ingredient is compressed into a tablet or in the form of a plurality of microtablets, particles, granules or non-perils. These microtablets, particles, granules or non-perils are then placed into a capsule or compressed into a capsule, possibly along with a granulation of the another active ingredient.

The dosage of the compounds of the present invention that will be most suitable for prophylaxis or treatment will vary with the form of administration, the particular compound chosen and the physiological characteristics of the particular patient under treatment. Generally, small dosages may be used initially and, if necessary, increased by small increments until the desired effect under the circumstances is reached. Generally speaking, oral administration may require higher dosages.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations. The dose may also be provided by controlled release of the compound, by techniques well known to those in the art.

Additional information regarding the preparation of the present compounds for administration and the formulation of compostions according to the present invention is provided infra.

The compounds useful in the methods of the present invention may be prepared in a number of ways well known to those skilled in the art. The compounds can be synthesized, for example, by the methods as described below, or variations thereon as appreciated by the skilled artisan. The reagents used in the preparation of the compounds of this invention can be either commercially obtained or can be prepared by standard procedures described in the literature. All processes disclosed in association with the present invention are contemplated to be practiced on any scale, including milligram, gram, multigram, kilogram, multikilogram or commercial industrial scale.

For compounds herein in which a variable appears more than once, each variable can be a different moiety selected from the Markush group defining the variable. For example, where a structure is described having two R groups that are simultaneously present on the same compound, the two R groups can represent different moieties selected from the Markush group defined for R.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

As used herein, the terms "component," "composition of compounds," "compound," "drug," "pharmacologically active agent," "active agent," "therapeutic," "therapy," "treatment," or "medicament" are used interchangeably herein to refer to a compound or compounds or composition of matter which, when administered to a subject (human or animal) induces a desired pharmacological and/or physiologic effect by local and/or systemic action.

The abbreviations in the specification correspond to units of measure, techniques, properties, or compounds as follows: "min" means minute(s), "g" means gram(s), "mg" means milligram(s), "µg" means microgram(s), "eq" means equivalent(s), "h" means hour(s), "µL" means microliter(s), "mL" means milliliter(s), "mM" means millimolar, "M" means molar, "mmol" or "mmole" means millimole(s), "cm" means centimeters, "SEM" means standard error of the mean, and "IU" means International Units. "$IC_{50}$ value" or "$IC_{50}$" means dose of the compound which results in 50% alleviation or inhibition of the observed condition or effect.

As used herein, "alkyl" refers to an optionally substituted, saturated straight, or branched, hydrocarbon radical having from about 1 to about 20 carbon atoms (and all combinations and subcombinations of ranges and specific numbers of carbon atoms therein). Where appropriate, "alkyl" can mean "alkylene"; for example, if X is —$R_1R_2$, and $R_1$ is said to be "alkyl", then "alkyl" may correctly be interpreted to mean "alkylene". In the present disclosure, the term "alkyl" or a shortened or otherwise modified version thereof (for example, as used in conjunction with another substituent, for example, in the case of "alkoxy" or "aminoalkyl") may be preceded by a range specifying the number of carbon atoms in the alkyl portion of the described moiety. For example, "amino($C_1$-$C_3$)alkyl" refers to the fact that the alkyl portion of the substituent possesses one to three carbon atoms.

"Amino" refers to —$NH_2$ and may include one or more substituents that replace hydrogen. "Amino" is used interchangeably with amine and is also intended to include any pharmaceutically acceptable amine salts. For example, amino may refer to —$NH^+(X)(Y)Cl^-$, wherein X and Y are preferably and independently hydrogen or alkyl, wherein alkyl may include one or more halo substitutions.

As used herein, "aryl", "arene", and "aromatic" each refer to an optionally substituted, saturated or unsaturated, monocyclic, polycyclic, or other homo- or heterocyclic aromatic ring system having from about 3 to about 50 ring members (and all combinations and subcombinations of ranges and specific numbers of carbon atoms therein), with from about 5 to about 10 ring atom members being preferred. Such moieties encompass (include) "heteroaryl" and "heteroarene" as defined infra. Where appropriate, "aryl" can mean "arene"; for example, if X is —$R_1R_2$, and $R_1$ is said to be "aryl", then "aryl" may correctly be interpreted to mean "arene".

As used herein, "alkenyl" refers to an alkyl radical having from about 2 to about 20 carbon atoms and one or more double bonds (and all combinations and subcombinations of ranges and specific numbers of carbon atoms therein), wherein alkyl is as previously defined. In some embodiments, it is preferred that the alkenyl groups have from about 2 to about 6 carbon atoms. Alkenyl groups may be optionally substituted.

As used herein, "aralkyl" refers to alkyl radicals bearing one or more aryl substituents and having from about 4 to about 50 carbon atoms (and all combinations and subcombinations of ranges and specific numbers of carbon atoms therein), wherein aryl and alkyl are as previously defined. In some preferred embodiments, the alkyl moieties of the aralkyl groups have from about 1 to about 4 carbon atoms. In other preferred embodiments, the alkyl moieties have from about 1 to about 3 carbon atoms. Aralkyl groups may be optionally substituted.

"Alkylamino" signifies alkyl-(NH)—, wherein alkyl is as previously described and NH is defined in accordance with the provided definition of amino. "Arylamino" represents aryl-(NH)—, wherein aryl is as defined herein and NH is defined in accordance with the provided definition of amino. Likewise, "aralkylamino" is used to denote aralkyl-(NH)—, wherein aralkyl is as previously defined and NH is defined in accordance with the provided definition of amino. "Alkylamido" refers to alkyl-CH(=O)NH—, wherein alkyl is as previously described. "Alkoxy" as used herein refers to the group R—O— where R is an alkyl group, and alkyl is as previously described. "Aralkoxy" stands for R—O—, wherein R is an aralkyl group as previously defined. "Alkylsulfonyl" means alkyl-$SO_2$—, wherein alkyl is as previously defined. "Aminooxy" as used herein refers to the group amino-(O)—, wherein amino is defined as above. "Aralkylaminooxy" as used herein is used to denote aryl-alkyl-aminooxy-, wherein aryl, alkyl, and aminooxy are respectively defined as provided previously.

As used herein, "alkylene" refers to an optionally branched or substituted bivalent alkyl radical having the general formula —$(CH_2)_n$—, where n is 1 to 10. Non-limiting examples include methylene, trimethylene, pentamethylene, and hexamethylene.

"Alkyleneamino" refers to —$(CH_2)_n$—NH—, where n is 1 to 10 and wherein the bivalent alkyl radical may be optionally branched or substituted, and the amino group may include one or more substituents that replace hydrogen.

As used herein, "heteroaryl" or "heteroarene" refers to an aryl radical wherein in at least one of the rings, one or more of the carbon atom ring members is independently replaced by a heteroatom group selected from the group consisting of S, O, N, and NH, wherein aryl is as previously defined. Heteroaryl/heteroarene groups having a total of from about 3 to about 14 carbon atom ring members and heteroatom ring members are preferred. Likewise, a "heterocyclic ring" is an aryl radical wherein one or more of the carbon atom ring members may be (but are not necessarily) independently replaced by a heteroatom group selected from the group consisting of S, O, N, and NH. Heterocyclic rings having a total from about 3 to 14 ring members and heteroatom ring members are preferred, but not necessarily present; for example, "heterocyclohexyl" may be a six-membered aryl radical with or without a heteroatom group.

"Halo" and "halogen" each refers to a fluoro, chloro, bromo, or iodo moiety, with fluoro, chloro, or bromo being preferred.

"Haloalkyl" signifies halo-alkyl- wherein alkyl and halo, respectively, are as previously described.

"Thiol" refers to —SH. "Thionyl" refers to =S.

"Nitroalkyl" refers to $NO_2$-alkyl- wherein alkyl is as previously described.

The phrase reading "[moiety] is absent" means that the substituents to which the moiety is attached may be directly attached to each other.

Typically, substituted chemical moieties include one or more substituents that replace hydrogen. Exemplary substituents include, for example, halo (e.g., F, Cl, Br, I), alkyl, cycloalkyl, alkylcycloalkyl, cycloalkylalkyl, alkenyl, alkynyl, aralkyl, aryl, heteroaryl, heteroaralkyl, spiroalkyl, heterocycloalkyl, hydroxyl (—OH), nitro (—$NO_2$), cyano (—CN), amino (—$NH_2$), —N-substituted amino (—NHR"), —N,N-disubstituted amino (—N(R")R"), oxo (=O), carboxy (—COOH), —O—C(=O)R", —C(=O)R", —OR", —C(=O)OR", -(alkylene)-C(=O)—OR", —NHC(=O)R", aminocarbonyl (—C(=O)$NH_2$), —N-substituted aminocarbonyl (—C(=O)NHR"), —N,N-disubstituted aminocarbonyl (—C(=O)N(R")R"), thiol (—SH), thiolato (—SR"), sulfonic acid (—$SO_3H$), phosphonic acid (—$PO_3H$), —P(=O)(OR")OR", —S(=O)R", —S(=O)$_2$R", —S(=O)$_2NH_2$, —S(=O)$_2$NHR", —S(=O)$_2$NR"R", —NHS(=O)$_2$R", —NR"S(=O)$_2$R", —$CF_3$, —$CF_2CF_3$, —NHC(=O)NHR", —NHC(=O)NR"R", —NR"C(=O)NHR", —NR"C(=O)NR"R", —NR"C(=O)R" and the like. In relation to the aforementioned substituents, each moiety R" can be, independently, any of H, alkyl, cycloalkyl, alkenyl, aryl, aralkyl, heteroaryl, or heterocycloalkyl, for example.

As used herein, the terms "treatment" or "therapy" (as well as different word forms thereof) includes preventative (e.g., prophylactic), curative or palliative treatment.

As employed above and throughout the disclosure the term "effective amount" refers to an amount effective, at dosages, and for periods of time necessary, to achieve the desired result with respect to the treatment of the relevant disorder, condition, or side effect. It will be appreciated that the effective amount of components of the present invention will vary from patient to patient not only with the particular compound, component or composition selected, the route of administration, and the ability of the components to elicit a desired response in the individual, but also with factors such as the disease state or severity of the condition to be alleviated, hormone levels, age, sex, weight of the individual, the state of being of the patient, and the severity of the pathological condition being treated, concurrent medication or special diets then being followed by the particular patient, and other factors which those skilled in the art will recognize, with the appropriate dosage ultimately being at the discretion of the attendant physician. Dosage regimens may be adjusted to provide the improved therapeutic response. An effective amount is also one in which any toxic or detrimental effects of the components are outweighed by the therapeutically beneficial effects. As an example, the compounds useful in the methods of the present invention are administered at a dosage and for a time such that the level of activation and adhesion activity of platelets is reduced as compared to the level of activity before the start of treatment.

Compounds described herein throughout, can be used or prepared in alternate forms. For example, many amino-containing compounds can be used or prepared as an acid addition salt. Often such salts improve isolation and handling properties of the compound. For example, depending on the reagents, reaction conditions and the like, compounds as described herein can be used or prepared, for example, as their hydrochloride or tosylate salts. Isomorphic crystalline forms, all chiral and racemic forms, N-oxide, hydrates, solvates, and acid salt hydrates, are also contemplated to be within the scope of the present invention.

Certain acidic or basic compounds of the present invention may exist as zwitterions. All forms of the compounds, including free acid, free base and zwitterions, are contemplated to be within the scope of the present invention. It is well known in the art that compounds containing both amino and carboxy groups often exist in equilibrium with their zwitterionic forms. Thus, any of the compounds described herein throughout that contain, for example, both amino and carboxy groups, also include reference to their corresponding zwitterions.

"Hydrate" refers to a compound of the present invention which is associated with water in the molecular form, i.e., in which the H—OH bond is not split, and may be represented, for example, by the formula $R.H_2O$, where R is a compound of the invention. A given compound may form more than one hydrate including, for example, monohydrates ($R.H_2O$) or polyhydrates ($R.nH_2O$ wherein n is an integer>1) including, for example, dihydrates ($R.2H_2O$), trihydrates ($R.3H_2O$), and the like, or hemihydrates, such as, for example, $R.n_{/2}H_2O$, $R.n_{/3}H_2O$, $R.n_{/4}H_2O$ and the like wherein n is an integer.

"Solvate" refers to a compound of the present invention which is associated with solvent in the molecular form, i.e., in which the solvent is coordinatively bound, and may be represented, for example, by the formula R.(solvent), where R is a compound of the invention. A given compound may form more than one solvate including, for example, monosolvates (R.(solvent)) or polysolvates (R.n(solvent)) wherein n is an integer>1) including, for example, disolvates (R.2(solvent)), trisolvates (R.3(solvent)), and the like, or hemisolvates, such as, for example, $R.n_{/2}$(solvent), $R.n_{/3}$(solvent), $R.n_{/4}$(solvent) and the like wherein n is an integer. Solvents herein include mixed solvents, for example, methanol/water, and as such, the solvates may incorporate one or more solvents within the solvate.

"Acid hydrate" refers to a complex that may be formed through association of a compound having one or more base moieties with at least one compound having one or more acid moieties or through association of a compound having one or more acid moieties with at least one compound having one or more base moieties, said complex being further associated with water molecules so as to form a hydrate, wherein said hydrate is as previously defined and R represents the complex herein described above.

As used herein, the terms "substitute" or "substitution" refer to replacing a hydrogen with a non-hydrogen moiety.

As used used herein, the term "optionally substituted" means that substitution is optional and therefore includes both unsubstituted and substituted atoms and moieties. A "substituted" atom or moiety indicates that any hydrogen on the designated atom or moiety can be replaced with a selection from the indicated substituent group, provided that the normal valency of the designated atom or moiety is not exceeded, and that the substitution results in a stable compound. For example, if a methyl group (i.e., $CH_3$) is optionally substituted, then 3 hydrogens on the carbon atom can be replaced with substituent groups.

The compounds described herein can be asymmetric (e.g., having one or more stereocenters). All stereoisomers, such as enantiomers, epimers, and diastereomers, are intended unless otherwise indicated. Compounds of the present invention that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. An example method includes fractional recrystallizaion using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention also include tautomeric forms, such as keto-enol tautomers.

Compounds of the invention can also include all isotopes of atoms occurring in the intermediates or final compounds. Isotopes include those atoms having the same atomic number but different mass numbers. For example, isotopes of hydrogen include tritium and deuterium.

Compounds of the invention are intended to include compounds with stable structures. As used herein, "stable compound" and "stable structure" are meant to indicate a compound that is sufficiently robust to survive isolation to a useful degree of purity from a reaction mixture, and formulation into an efficacious therapeutic agent.

The phrase "pharmaceutically acceptable" is employed herein to refer to those compounds, materials, compositions, and/or dosage forms which are, within the scope of sound medical judgement, suitable for use in contact with the tissues of human beings and/or animals with acceptable levels of toxicity, irritation, allergic response, or other problem or complication, commensurate with a reasonable benefit/risk ratio.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts or the quaternary ammonium salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in, for example, *Remington's Pharmaceutical Sciences*, 17th ed., Mack Publishing Company, Easton, Pa., 1985, p. 1418 and *Journal of Pharmaceutical Science*, 66, 2 (1977), each of which is incorporated herein by reference in its entirety. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. These physiologically acceptable salts are prepared by methods known in the art, e.g., by dissolving the free amine bases with an excess of the acid in aqueous alcohol, or neutralizing a free carboxylic acid with an alkali metal base such as a hydroxide, or with an amine.

The present invention also includes prodrugs of the compounds described herein. As used herein, "prodrugs" refer to any covalently bonded carriers which release the active parent drug when administered to a mammalian subject. Prodrugs can be prepared by modifying functional groups present in the compounds in such a way that the modifications are cleaved, either in routine manipulation or in vivo, to the parent compounds. Prodrugs include compounds wherein hydroxyl, amino, sulfhydryl, or carboxyl groups are bonded to any group that, when administered to a mammalian subject, cleaves to form a free hydroxyl, amino, sulfhydryl, or carboxyl group respectively. Examples of prodrugs include, but are not limited to, acetate, formate and benzoate derivatives of alcohol and amine functional groups in the compounds of the invention. Preparation and use of prodrugs is discussed in, for example, T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are hereby incorporated by reference in their entirety.

When any variable occurs more than one time in any constituent or in any formula, its definition in each occurrence may be independent of its definition at every other occurrence. Combinations of substituents and/or variables are permissible only if such combinations result in stable compounds.

The term "administering" means either directly administering a compound or composition of the present invention, or administering a prodrug, derivative or analog which will form an equivalent amount of the active compound or substance within the body.

"Dosage unit" refers to physically discrete units suited as unitary dosages for the particular individual to be treated. Each unit may contain a predetermined quantity of active compound(s) calculated to produce the desired therapeutic effect(s) in association with the required pharmaceutical carrier. The specification for the dosage unit forms of the invention may be dictated by (a) the unique characteristics of the active compound(s) and the particular therapeutic effect(s) to be achieved, and (b) the limitations inherent in the art of compounding such active compound(s).

"Subject" or "patient" refers to an embryonic, immature, or adult animal, including the human species, that is treatable with the compositions, and/or methods of the present invention.

The present invention is further defined in the following Examples. It should be understood that these examples, while indicating preferred embodiments of the invention, are given by way of illustration only, and should not be construed as limiting the appended claims. From the above discussion and these examples, one skilled in the art can ascertain the essential characteristics of this invention, and without departing from the spirit and scope thereof, can make various changes and modifications of the invention to adapt it to various usages and conditions.

General Synthesis

All chemicals for use in preparing the inventive compounds were purchased from commercial vendors and used without further purification, unless otherwise noted.

Synthesis of some preferred embodiments was accomplished as illustrated in the following generalized schematics and as described below:

The compounds of the present invention can be prepared in a variety of ways known to one skilled in the art of organic synthesis. The compounds of the present invention can be synthesized using the methods as hereinafter described below, together with synthetic methods known in the art of synthetic organic chemistry or variations thereon as appreciated by those skilled in the art.

The compounds of this invention can be prepared from readily available starting materials using the following general methods and procedures. It will be appreciated that where typical or suitable process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

The processes described herein can be monitored according to any suitable method known in the art. For example, product formation can be monitored by spectroscopic means, such as nuclear magnetic resonance spectroscopy (e.g., $^1$H or $^{13}$C NMR), infrared spectroscopy (IR), spectrophotometry (e.g., UV-visible), or mass spectrometry, or by chromatography such as high performance liquid chromatography (HPLC) or thin layer chromatography.

Preparation of compounds can involve the protection and deprotection of various chemical groups. The need for protection and deprotection, and the selection of appropriate protecting groups can be readily determined by one skilled in the art. The chemistry of protecting groups can be found, for example, in Greene, et al., Protective Groups in Organic Synthesis, 2d. Ed., Wiley & Sons, 1991, which is incorporated herein by reference in its entirety.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

The compounds of the invention can be prepared, for example, using the reaction pathways and techniques as described below.

As shown in Scheme 1, alcohol 1-1 (wherein n can be, for example, 0 or 1; and Pg$^1$ is an amine protecting group (such as tert-butyloxycarbonyl or BOC; or acetyl; or CBZ)) can be reacted with a halogenating reagent such as (diethylamino) sulfur trifluoride (DAST) to afford the halogenated (fluorinated) 1-2. The protecting group Pg$^1$ of compound 1-2 can be removed under suitable conditions to afford compound 1-3. Those skilled in the art would readily choose suitable conditions depending on the protecting group Pg$^1$ used, for example, acid conditions can be used to remove Boc. The amine can be oxidized with mCPBA in refluxing DCE (1,2-dichloroethane) to give the desired nitro compound 1-4. Proper protection of amino group of 1-1 can give 1-5, which can be methylated to give 1-6. Removal of protection groups can afford to 1-7.

Scheme 1

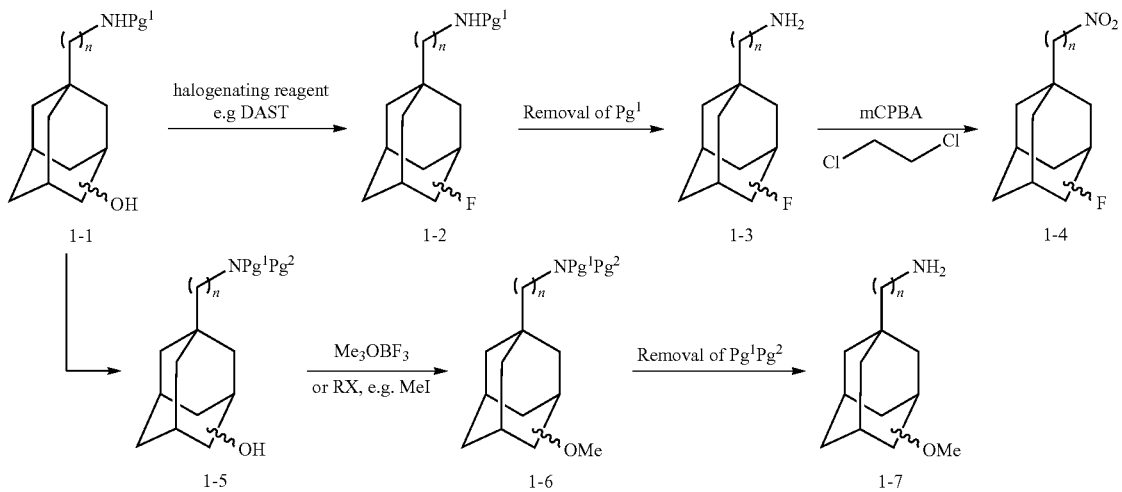

n = 0, 1

As shown in Scheme 2, ketone 2-1 (wherein n can be, for example, 0 or 1; and $Pg^1$ is an amine protecting group (such as tert-butyloxycarbonyl or BOC; or acetyl or CBZ)) can be oxidized with Dess-Martine periodinane to afford ketone 2-2. Treatment of ketone 2-2 with Lawesson's reagent can give thioketone 2-3. The protecting group $Pg^1$ of compound 2-3 can be removed under suitable conditions to afford compound 2-4. Thioketone 2-3 can be reduced to thiol 2-5 by using a suitable such as metal borohydride (e.g. sodium borohydride). The protecting group $Pg^1$ of compound 2-5 can be removed under suitable conditions to afford compound 2-6. 2-2 reacts with hydroxylamine gives oxime 2-7. The protecting group $Pg^1$ of compound 2-7 can be removed under suitable conditions to afford compound 2-8.

Scheme 2

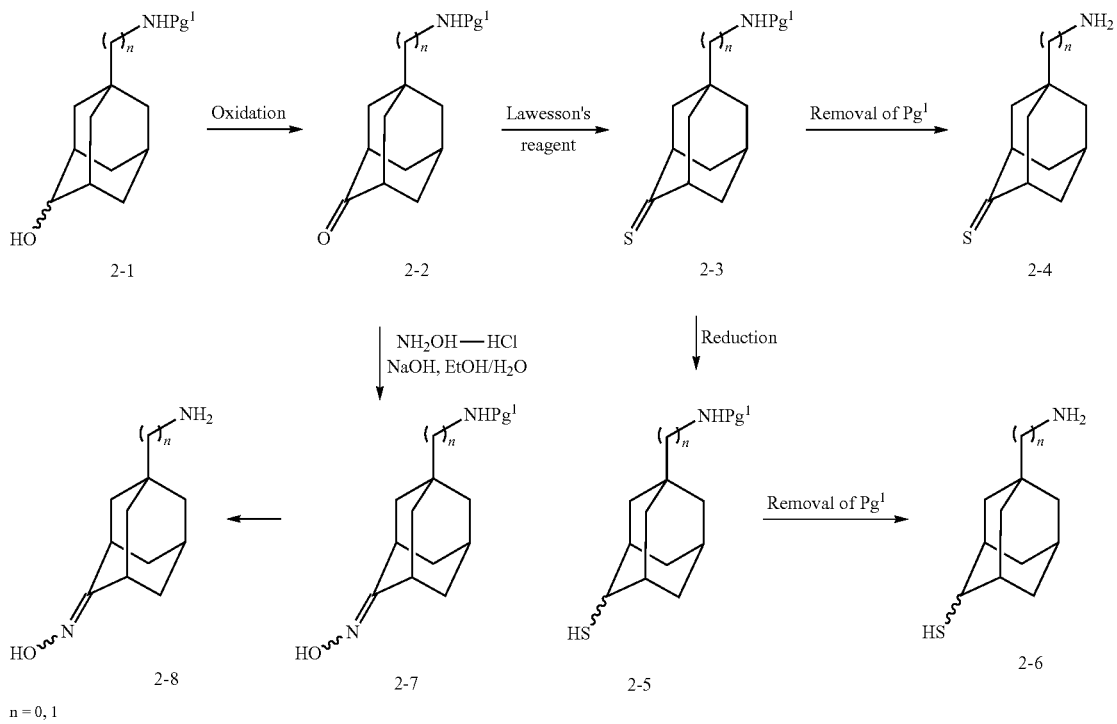

As shown in Scheme 3, ketone 3-1 ($Pg^1$ is an amine protecting group (such as tert-butyloxycarbonyl or BOC; or acetyl)) can be reacted with Tosmic/KO$^t$Bu to give nitrile 3-2.

The protecting group $Pg^1$ of nitrile 3-2 can be removed under suitable conditions to afford compound 3-5. Nitrile 2-2 can be also reduced to aldehyde 3-3 by using a suitable such as metal borohydride (e.g. DIBAL-H). Aldehyde 2-3 can be reacted with a halogenating reagent such as (diethylamino) sulfur trifluoride (DAST) to afford the halogenated (fluorinated) 3-4. The protecting group $Pg^1$ of compound 2-4 can be removed under suitable conditions to afford compound 3-6.

Scheme 3

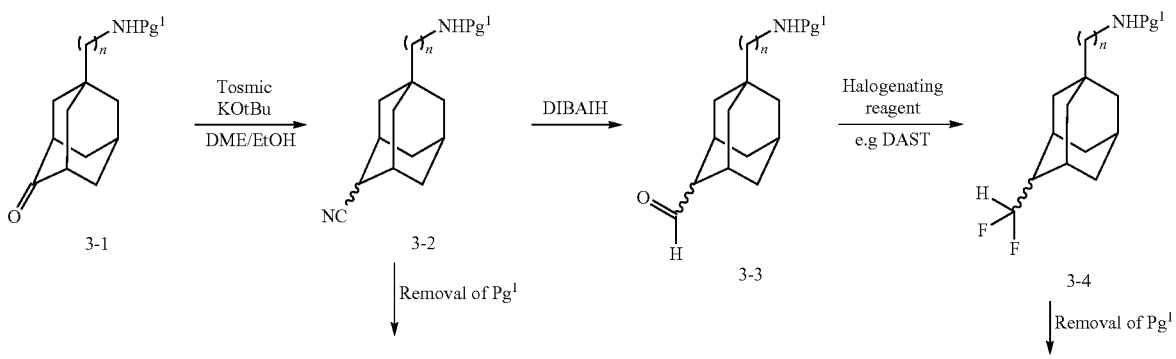

3-5 n = 0, 1

3-6

As shown in Scheme 4, ketone 4-1 (Pg$^1$ is an amine protecting group (such as tert-butyloxycarbonyl or BOC; or acetyl)) can react with metallic reagents such as MeLi or MeMgBr to give alcohol 4-2. The protecting group Pg$^1$ of compound 4-2 can be removed under suitable conditions to afford compound 4-5. Alcohol 4-2 can react with a halogenating reagent such as (diethylamino) sulfur trifluoride (DAST) to afford the halogenated (fluorinated) 4-3. The protecting group Pg$^1$ of compound 4-3 can be removed under suitable conditions to afford compound 4-4.

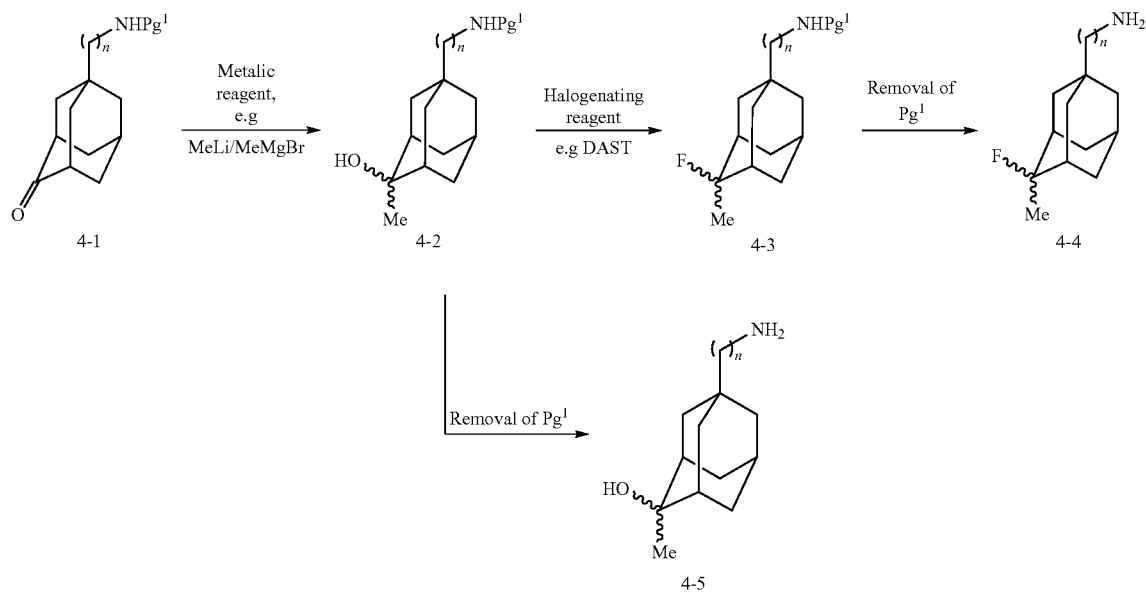

Scheme 4 n = 0, 1

As shown in Scheme 5, ketone 5-1 (Pg$^1$ is an amine protecting group (such as tert-butyloxycarbonyl or BOC; or acetyl)) can react with a diol such as Ethane-1,2-diol to give dioxolane 5-2. The protecting group Pg$^1$ of compound 5-2 can be removed under suitable conditions to afford compound 5-3. ketone 5-1 can react with a halogenating reagent such as (diethylamino) sulfur trifluoride (DAST) to afford the halogenated (fluorinated) 5-4. The protecting group Pg$^1$ of compound 5-4 can be removed under suitable conditions to afford compound 5-5.

Scheme 5

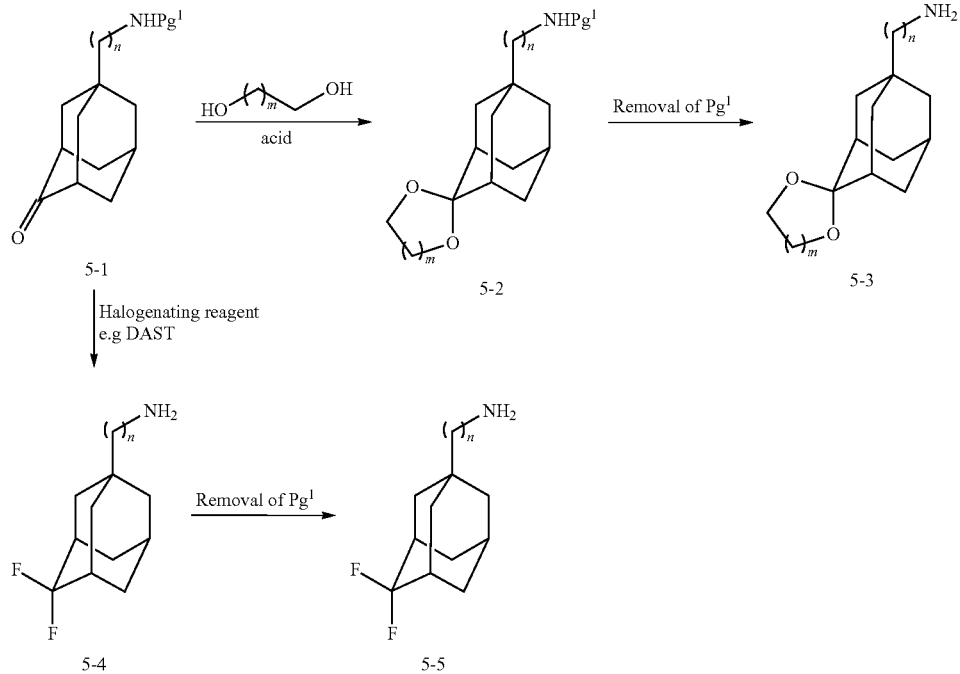

n = 0, 1
m = 1, 2

As shown in Scheme 6, known alchol 6-1 (*J. Med. Chem.* 2007, 50, 149-164) can be selectively protected with Pg$^1$ (Pg$^1$ is an amine protecting group (such as tert-butyloxycarbonyl or BOC; or acetyl)) to give 6-2. Oxidation of 7-2 can give ketone 6-3, which reacts with a metalic reagent, such as MeLi can give alcohol 6-4. The protecting group Pg$^1$ of compound 6-4 can be removed under suitable conditions to afford compound 6-5. Halogenation of 6-2 followed by deprotection can give 6-7. Condensation of 6-1 and formaldehyde can afford 6-6.

Scheme 6

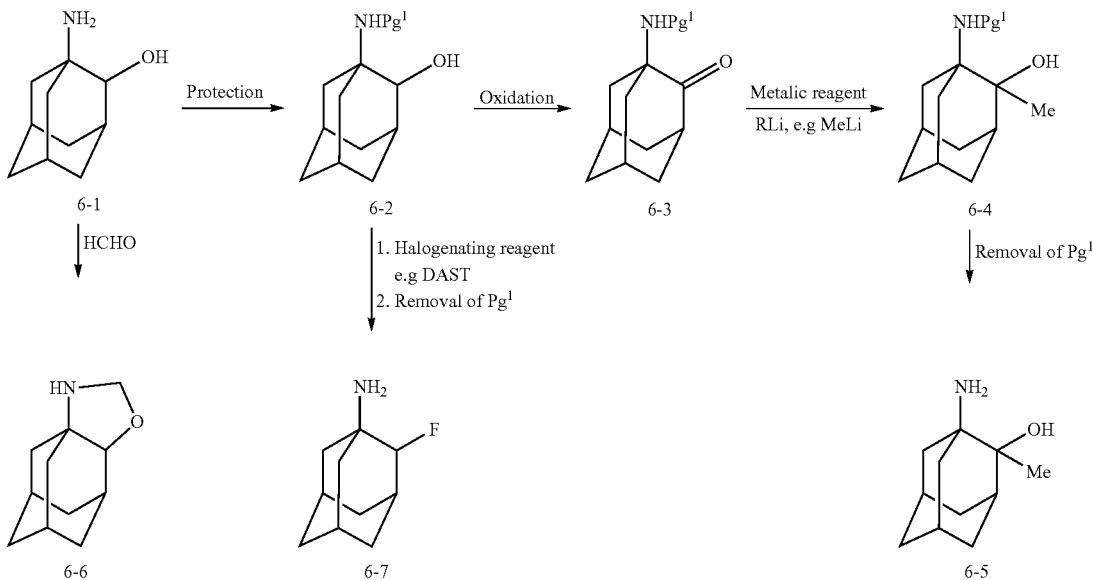

Additional starting materials and intermediates useful for making the compounds of the present invention can be obtained from chemical vendors such as Sigma-Aldrich or can be made according to methods described in the chemical art.

Those skilled in the art can recognize that in all of the schemes described herein, functional (reactive) groups (including those on a substituent group such as $X^2$, $X^3$, $Y^1$, $Y^2$, etc., if present) can undergo further modification if appropriate and/or desired. For example, an OH group (such as the one in compound 1-1 or 2-3) can be converted into a better leaving group such as mesylate, which in turn is suitable for nucleophilic substitution, such as by CN or an azide group. For another example, a CN group can be hydrolyzed to afford an amide group or a carboxylic acid group; a carboxylic acid can be converted to an amide (for example, by standard coupling reactions with another amine (such as in the presence of an amide coupling reagent such BOP, HBTU, HATU, EDC, or DCC), and in the presence of a suitable base such as triethylamine, diisopropylethylamine, N-methylmorpholine, or N—N-dimethylaminopyridine); a carboxylic acid can be converted to an ester, which in turn can be reduced to an alcohol, which in turn can be further modified. For another example, an azide group can be reduced to an amino group. In some embodiments, a primary amine or a secondary amine moiety (present on a part of the compound of invention) can be converted to amide, sulfonamide, urea, or thiourea moiety by reacting it with an appropriate reagent such as an acid chloride, a sulfonyl chloride, an isocyanate, or a thioisocyanate compound. In some embodiments, a primary amine, a secondary amine, or a tertiary amine moiety (such as those present on part of the compound of invention) can be alkylated to form a quaternary ammonium salt. One skilled in the art will recognize further such modifications.

The compounds provided herein that contain one or more chiral centers can be prepared as racemates or mixtures of various stereoisomers. The stereoismers can further be separated. In addition, individual stereisomer can be prepared by chiral synthesis known to those skilled in the art. Different steroisomers may differ in pharmacological activity.

As used herein, the term "reacting" refers to the bringing together of designated chemical reactants such that a chemical transformation takes place generating a compound different from any initially introduced into the system. Reacting can take place in the presence or absence of solvent.

As provided above, when employed as pharmaceuticals, the compounds of the invention can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

The present invention also includes pharmaceutical compositions which contain, as the active ingredient, one or more of the compounds of the invention above in combination with one or more pharmaceutically acceptable carriers. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 1 to about 100 mg, from about 5 to about 75 mg, from about 5 to about 50 mg, from about 10 to about 30 mg, or from about 10 to about 20 mg of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compounds of the invention can also be formulated in combination with one or more additional active ingredients which can include any pharmaceutical agent such as anti-viral agents (including Tamiflu), antibodies, immune suppressants, anti-inflammatory agents, and the like.

Labeled Compounds and Assay Methods

Another aspect of the present invention relates to labeled compounds of the invention (radio-labeled, fluorescent-labeled, colloidal gold-labeled, etc.) that would be useful not only in radio-imaging but also in assays, both in vitro and in vivo, for localizing and quantitating the virus in tissue samples, including human, and for identifying binding sites by inhibition binding of a labeled compound. Accordingly, the present invention includes enzyme assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^{2}$H (also written as D for deuterium), $^{3}$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. The radionuclide that is incorporated in the instant radio-labeled compounds will depend on the specific application of that radio-labeled compound. For example, for in vitro receptor labeling and competition assays, compounds that incorporate $^{3}$H, $^{14}$C, $^{82}$Br, $^{125}$I, $^{131}$I, $^{35}$S or will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is understood that a "radio-labeled compound" is a compound that has incorporated at least one radionuclide. In some embodiments the radionuclide is selected from $^{3}$H, $^{14}$C, $^{125}$I, $^{35}$S and $^{82}$Br.

In some embodiments, the labeled compounds of the present invention contain a fluorescent label, which are widely known to those skilled in the art.

Synthetic methods for incorporating radio-isotopes and fluorescent labels into organic compounds are well known in the art.

A labeled compound of the invention (radio-labeled, fluorescent-labeled, etc.) can be used in a screening assay to identify/evaluate compounds. For example, a newly synthesized or identified compound (i.e., test compound) which is labeled can be evaluated for its ability to bind a virus by monitering its concentration variation when contacting with the virus, through tracking the labeling. For another example, a test compound (labeled) can be evaluated for its ability to reduce binding of another compound which is known to bind to a virus (i.e., standard compound). Accordingly, the ability of a test compound to compete with the standard compound for binding to the virus (e.g. M2 protein of an influenza virus) directly correlates to its binding affinity. Conversely, in some other screening assays, the standard compound is labled and test compounds are unlabeled. Accordingly, the concentration of the labled standard compound is monitored in order to evaluate the competition between the standard compound and the test compound, and the relative binding affinity of the test compound is thus ascertained.

Kits

The present invention also includes pharmaceutical kits useful, for example, in the treatment or prevention of a viral infection disorder referred to herein which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results. Certain compounds of the Examples were found to be inhibitors of viroporins (e.g. M2 protein of an influenza virus) according to one or more of the assays provided herein.

EXAMPLES

Example 1 and 2

C-(4-Fluoro-adamantan-1-yl)-methylamine (1 and 2)

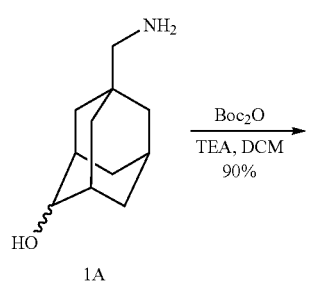

Step 1.
(4-Hydroxy-adamantan-1-ylmethyl)-carbamic acid tert-butyl ester (1B)

At 0° C., to a solution of 5-aminomethyl-adamantan-2-ol hydrochloride salt 1A (3.25 g, 15 mmol) in dichloromethane (DCM, 100 mL) were added triethylamine (TEA, 3 mL). Boc$_2$O (3.92 g, 18 mmol) in DCM (10 mL) was added to above solution slowly. The resulting solution was stirred at room temperature (rt) for 10 hours before it was quenched by 50 ml of NH$_4$Cl aq (Sat'd) solution. The mixture was extracted by DCM (100 mL×3) and the combined DCM layers were dried over Na$_2$SO$_4$. Solvent was remove under vacuum gave the title compound 1B as a solid (3.8 g, 90%), which as used to next step without further purification. LC-MS (ESR): m/z=282 (M+H)$^+$.

Step 2. (4-Fluoro-adamantan-1-ylmethyl)-carbamic acid tert-butyl ester (1C and 2C)

At −78° C., to a solution of (diethylamino)sulfur trifluoride (DAST) (137 mg, 0.854 mmol) in DCM (5 mL) was added (4-Hydroxy-adamantan-1-ylmethyl)-carbamic acid tert-butyl ester 1B (200 mg, 0.711 mmol) in DCM (1 mL) dropwise. The reaction mixture was stirred at rt for 1 hour before it was quenched by 2 ml of NH$_4$Cl aq (Sat'd) solution. The mixture was extracted by DCM (5 mL×3) and the combined organic extracts were dried over Na$_2$SO$_4$. Solvents were remove under vacuum and the residue was purified by silica gel chromatography (0 to 5% of MeOH in DCM:Hexane 1:1(v/v)) to give 50 mg and 60 mg of 1C (less polar) and 2C (more polar) respectively as a pair of equatorial and axial isomers (80%). LC-MS (ESR): m/z=283 (M+H)$^+$.

Step 3. C-(4-Fluoro-adamantan-1-yl)-methylamine (1 and 2)

To each of above tert-butyl esters 1C and 2C (30 mg, 0.16 mmol) in 2 mL of 1,4-dioxane was added HCl (4 N in 1,4-dioxane, 1.0 mL, 4.0 mmol). The mixture was stirred at rt for overnight. The solvent was removed under vacuum. The resulting residue was dissolved in 2 mL of water and was washed with EtOAc (5 mL×3). The water was the removed under vacuum to give the title compound as hydrogen chloride salts 1 and 2 (16 mg and 15 mg respectively) respectively. LC-MS (ESR): m/z=184 (M+H)$^+$. Less polar one 1: $^1$H NMR (300 MHz, CD$_3$OD) δ 4.77-4.73 (m, 1H), 4.60-4.56 (m, 1H), 2.63 (brs, 2H), 2.27-2.20 (m, 2H), 2.00-1.68 (m, 7H), 1.58 (brs, 2H), and 1.449-1.374 (m, 2H). More Polar one 2: $^1$H NMR (300 MHz, CD$_3$OD) δ 4.48-4.74 (m, 1H), 4.61-4.56 (m, 1H), 2.67 (br s, 2H), 2.22-1.95 (m, 5H), 1.74-1.49 (m, 8H).

Example 3 and 4

5-Aminomethyl-2-methyl-adamantan-2-ol (3 and 4)

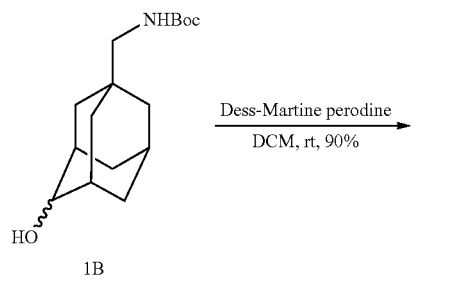

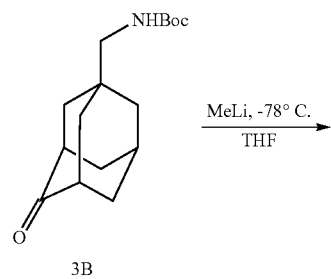

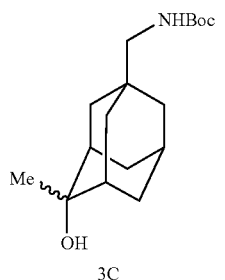

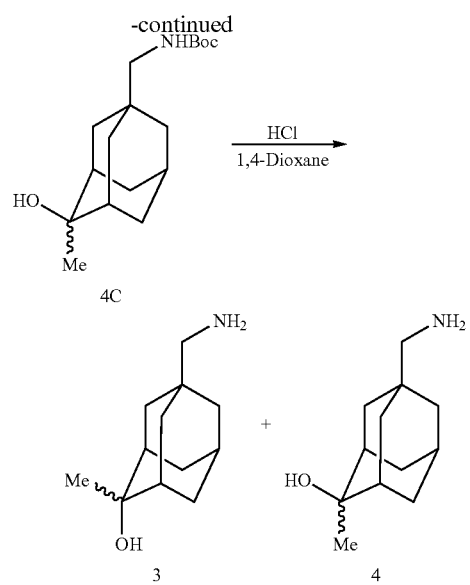

Step 1. (4-Oxo-adamantan-1-ylmethyl)-carbamic acid tert-butyl ester (3B)

To a solution of (4-Hydroxy-adamantan-1-ylmethyl)-carbamic acid tert-butyl ester (1B) (2.81 g, 10 mmol) in 200 mL of DCM was added Dess martin periodinane (5.08 g, 12 mmol) at one portion at rt. The mixture was stirred at rt overnight and was quenched by 20 mL of NH$_4$Cl aq (Sat'd) solution. The mixture was extracted by DCM (5 mL×3) and the combined DCM layers were dried over Na$_2$SO$_4$. Solvent was remove under vacuum and the residue was purified by silica gel chromatography (Hexane:EtOAc 2:1(v/v)) to give the title compounds (3B) (2.52 g, 90%). LC-MS (ESR): m/z=280 (M+H)$^+$.

Step 2. (4-Hydroxy-4-methyl-adamantan-1-ylmethyl)-carbamic acid tert-butyl ester (3C and 4C)

At −78° C., to a solution of (4-Oxo-adamantan-1-ylmethyl)-carbamic acid tert-butyl ester 3B (500 mg, 1.79 mmol) in 10 mL of THF was added MeLi (1.6 M in ether, 5 mL, 8.0 mmol) dropwise. The mixture was stirred at −78° C. for 30 minutes before it was quenched by 5 mL of NH$_4$Cl aq (Sat'd) solution. The mixture was extracted by DCM (5 mL×3) and the combined DCM layers were dried over Na$_2$SO$_4$. Solvent was remove under vacuum and the residue was purified by silica gel chromatography [0 to 5% of MeOH in DCM:Hexane 1:1(v/v)] to give the title compounds 3C (less polar) and 4C (more polar) as a pair of equatorial and axial isomers (120 mg and 110 mg isomerically pure). LC-MS (ESR): m/z=296 (M+H)$^+$.

Step 3. 5-Aminomethyl-2-methyl-adamantan-2-ol (3 and 4)

To each of 3C and 4C (30 mg, 0.10 mmol) in 2 mL of 1,4-dioxane was added HCl (4N in 1,4-dioxane, 1.0 mL). The mixture was stirred at rt for overnight. The solvent was removed under vacuum. The resulting residue was dissolved in 2 mL of water and was washed with EtOAc (5 mL×3). The water was the removed under vacuum to give the title compound as hydrogen chloride salts (3 and 4) respectively (19 mg and 17 mg respectively). LC-MS (ESR): m/z=196 (M+H)$^+$. Less polar one 3: $^1$HNMR (300 MHz, CD$_3$OD) δ 2.64 (s, 2H), 2.34-2.29 (m, 2H), 1.96-1.91 (m, 2H), 1.79-1.7 (m, 4H), 1.60-1.40 (m, 6H), and 1.32 (s, 3H). More polar one 4: $^1$HNMR (300 MHz, CD$_3$OD) δ 3.35 (s, 1H), 2.62 (s, 2H), 2.16-2.06 (m, 2H), 1.98-1.87 (m, 2H), 1.77 (br s, 2H) 1.71-1.63 (m, 2H), 1.54 (br s, 2H), 1.35 (s, 3H) and 1.31 (s, 1H).

Example 5 and 6

4-Fluoroadamantan-1-amine (5 and 6)

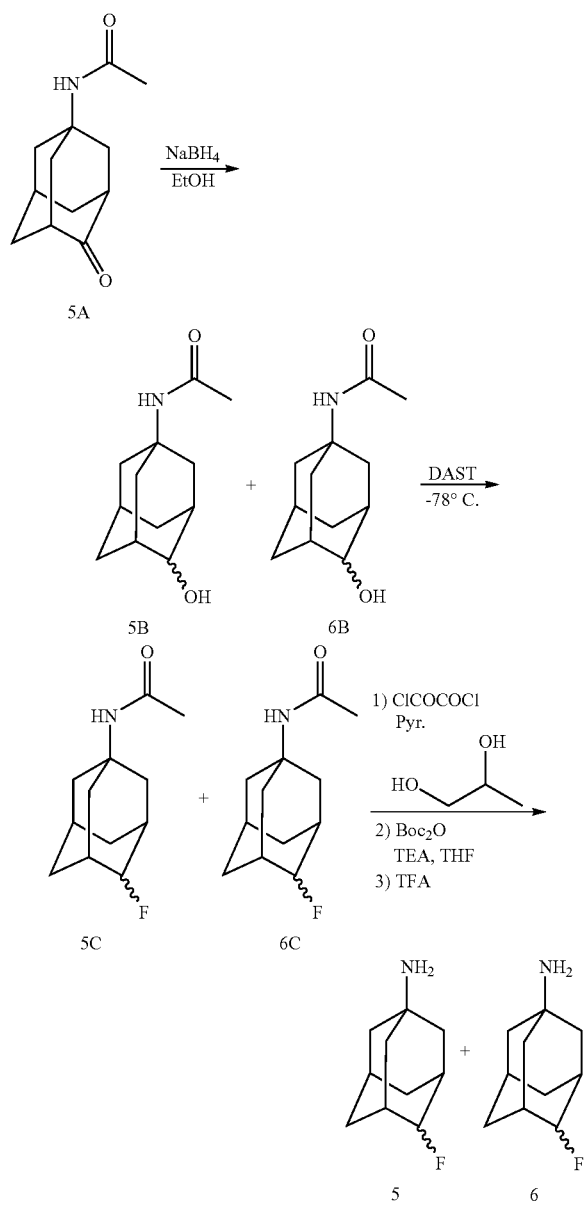

Step 1. N-(4-hydroxy-1-adamantyl)acetamide (5B and 6B)

819.8 mg of Ketone A1 in 50 ml of absolute EtOH was added NaBH$_4$ in portions at rt. The reaction was stirred for 45 minutes, at which time the solution was carefully quenched with water. The reaction mixture was extracted with EtOAc twice and the organic phases were combined, dried (anhydrous Na$_2$SO$_4$), and concentrated. The crude mixture was purified by column chromatography (0~5% MeOH in EtOAc) to yield 360.6 mg of the desired mixture of alcohols 5B and 6B. LC-MS (ESR): m/z=210.3 (M+H)$^+$, 232.2 (M+Na)$^+$.

Step 2. N-(4-fluoro-1-adamantyl)acetamide (5C and 6C)

To a mixture of alcohols 5B and 6B (350.0 mg) in 10 ml of DCM at −78° C. was added dropwise of DAST (0.40 ml) for a period of 10 minutes. The reaction mixture was stirred at −78° C. for 15 min and then slowly warmed to rt and continued stirring for an additional 2 hours. The reaction was carefully quenched with water extracted with EtOAc twice. The organic phases were combined, dried (anhydrous Na$_2$SO$_4$), and concentrated. The crude mixture was purified by column chromatography (0~60% EtOAc in hexane) to yield 62.1 and 50.1 mg of the desired product 5C (less polar isomer) and 6C (more polar isomer), respectively. Data of 5C, 212.3 (M+H)$^+$; LC-MS (ESR): m/z=210.3 (M+H)$^+$, 232.2 (M+Na)$^+$. 5C: LC-MS (ESR): M/Z=212.3 (M+H)$^+$.

Step 3. 4-Fluoroadamantan-1-amine (5 and 6)

A solution of amide 5C (55.4 mg) in dry THF (3 ml) was treated with 0.04 ml of pyridine and cooled to 0° C. Oxalyl chloride (0.16 ml, 2.0M in DCM) was added dropwise. After stirring at 0° C. for 45 minutes, 1,2-propyldiol (0.05 ml) was added in one portion and the reaction was warmed to rt. The reaction mixture was diluted with EtOH and then concentrated under reduced pressure. The crude oil was partitioned between HCl (1M) and methyl t-butyl ether (MtBE, 10 ml). The organic phase was washed with 1.0 M of HCl solution. The combined aqueous layer were basified with 4N NaOH to pH 11, and the basified mixture was then extracted EtOAc twice. The organic phases were combined, dried (over anhydrous Na$_2$SO$_4$), and concentrated.

The crude material formed above was dissolved in 3 ml of THF. Boc-anhydride (100.9 mg) and TEA (0.5 ml) was added sequentially and the resulting mixture was stirred at rt for 2 hrs before it was quenched with NaHCO$_3$ solution. The aqueous mixture was extracted with EtOAc twice. The combined organic phase was dried (anhydrous Na$_2$SO$_4$), and concentrated. The crude mixture was purified by column chromatography (0~15% EtOAc in hexane) to yield 44.4 mg of the Boc-protected desired product 5.

A 1.5 ml of DCM solution of Boc-protected 5 (44.4 mg) was added 1.5 ml of TFA and was stirred for 30 minutes. LC-MS indicated that the reaction was completed. The reaction mixture was condensed by rotary evaporation under high vacuum at rt. The residue was then washed with dry ether three times. The off white solid formed was under high vacuum for overnight. The yield is 45.0 mg (5). LC-MS (ESR): m/z=170.1 (M+H)$^+$. 22.5 mg of 6 was prepared under the similar reaction condition above. LC-MS (ESR): m/z=170.1 (M+H)$^+$.

Example 7

5-Amino-adamantane-2-carbonitrile (7)

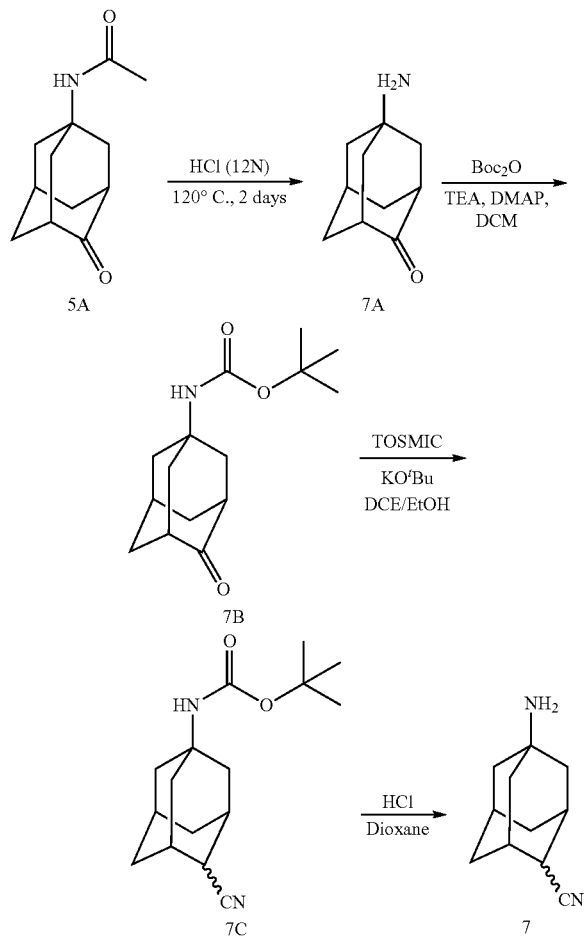

Step 1. Synthesis of 5-aminoadamantan-2-one (1B)

A solution of N-(4-oxoadamantan-1-yl)acetamide (5A) (20 mmol) in 200 mL of concentrated, aqueous HCl was heated in a sealed pressure tube at 130° C. for 20 h. The solvent was removed under reduced pressure to give amine 7A as an HCl salt in 90% yield as an off-white solid. Data: LC/MS (ESR) m/z 166 [M+H]$^+$.

Step 2. Synthesis of tert-Butyl (4-oxoadamantan-1-yl)carbamate (7B)

At 0° C., to a suspension of amine 7A (15 mmol) in DCM (100 mL) was added triethylamine (TEA, 3 mL). A solution of Boc$_2$O (18 mmol) in DCM (10 mL) was added slowly and the reaction mixture was maintained at rt for 10 h. The reaction was diluted with a saturated, aqueous NH$_4$Cl solution (50 mL) and the layers were separated. The aqueous layer was extracted with DCM (3×100 mL) and the combined organic layers were dried (Na$_2$SO$_4$). The solvent was remove under vacuum to provide the carbamate 7B in 90% yield as a solid. The material was used in the next step without further purification. Data: LC/MS (ESR) m/z 266 [M+H]$^+$.

Step 3: (4-Cyano-adamantan-1-yl)-carbamic acid tert-butyl ester (7C)

Solid t-BuOK (260 mg, 2.32 mmol) was added as 6 portions to a solution of ketone 8A (300 mg, 1.13 mmol) and TosMIC (300 mg, 1.54 mmol) in a mixture of DME (5.0 mL) and absolute EtOH (1 mL) while keeping the temperature between 5 and 10° C. The reaction mixture was allowed to warm to rt and was maintained for 30 min. The reaction mixture was then heated at 35-40° C. for 30 min and was then allowed to cool to rt. The precipitate (TosK) was removed by filtration and the filter cake was washed with DME. The combined organic layers were concentrated and the residue was purified by column chromatography (0~35% EtOAc in hexane) to provide nitrile 7C (190 mg, 63%). Data: LC/MS (ESR) m/z 277 [M+H]$^+$.

Step 4: 5-Amino-adamantane-2-carbonitrile (7)

To 7C (30 mg, 0.10 mmol) in 2 mL of 1,4-dioxane was added HCl (4N in 1,4-dioxane, 1.0 mL). The mixture was stirred at rt for overnight. The solvent was removed under vacuum. The resulting residue was dissolved in 2 mL of water and was washed with EtOAc (5 mL×3). The water was the removed under vacuum to give the title compound as hydrogen chloride salts (7) respectively (20 mg). LC-MS (ESR): m/z=177 (M+H)$^+$

Example 8

4,4-Difluoro-adamantan-1-ylamine (8)

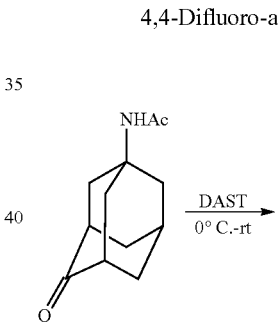

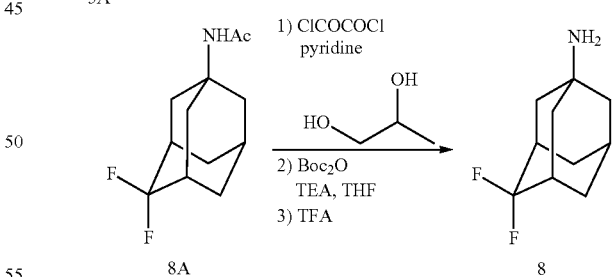

Step 1. Synthesis of (8A)

To a solution of 321.4 mg of the ketone 5A in 10 ml of benzene was added 0.3 ml of DAST dropwise for a period of 10 min. The resulting mixture was heated to 50° C. for overnight when the reaction was quenched by the addition of NaHCO$_3$ aqueous solution. The reaction mixture was extracted with EtOAc twice and the organic phases were combined, dried (over anhydrous Na$_2$SO$_4$), and concentrated.

The crude mixture was purified by column chromatography (0~60% EtOAc in Hexane) to yield 171.2 mg of 8A. LC/MS (ESR) m/z=230.1 [M+H]⁺.

Step 2. Synthesis of (8)

A 2.0 M solution of oxalyl chloride in DCM (0.30 mL) was added dropwise to a solution of amide 8A (118.0 mg) in dry THF (4 mL) and pyridine (0.06 mL) at 0° C. The reaction mixture was maintained at 0° C. for 45 min when 1,2-propanediol (0.081 mL) was added in one portion and the reaction was allowed to warm to rt. The reaction mixture was diluted with EtOH (5 mL) and was concentrated. The crude oil was partitioned between 1 M aqueous HCl and TBME (10 mL) and the layers were separated. The organic phase was extracted with 1.0 M aqueous HCl solution (1×) and the pH of the combined aqueous layers was adjusted to pH 11 with 4 N aqueous NaOH. The aqueous layer was then extracted EtOAc (2×) and the combined organic layers were dried ($Na_2SO_4$), and concentrated to provide the crude amine.

Boc-anhydride (485.6 mg) and TEA (0.3 mL) was added sequentially to a solution of the crude amine in THF (10 mL) and the reaction mixture was maintained at rt for 2 h. The reaction mixture was diluted with $NaHCO_3$ solution and the aqueous layer was extracted with EtOAc (2×). The combined organic layers were dried ($Na_2SO_4$) and concentrated. The residue was purified by silica gel chromatography (0/100 to 16/84 EtOAc/hexane) to provide 111.0 mg of the pure carbamate. LC/MS (ESR) m/z 288.2 [M+H]⁺, 310.4 [M+Na]⁺.

The pure carbamate (99.9 mg) in 2.0 ml of DCM was treated with 2.0 ml of TFA at rt and the reaction mixture was maintained at rt for 2 h. The reaction mixture was concentrated and the residue was triturated with ether (3×) and dried to provide 70.1 mg of amine 8 as a white solid. LC/MS (ESR) m/z=188.2 [M+H]⁺.

Example 9

4-Fluoro-4-methyl-adamantan-1-ylamine

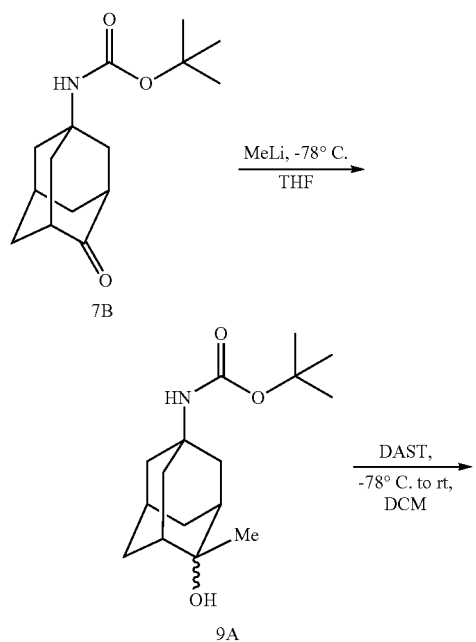

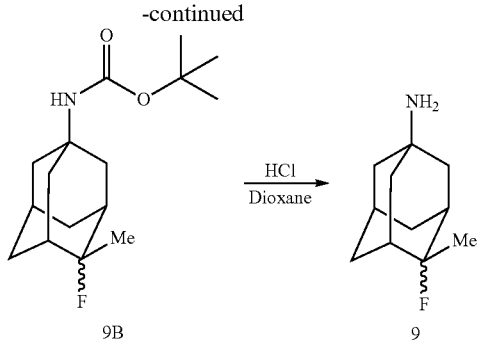

Step 1: (4-Hydroxy-4-methyl-adamantan-1-yl)-carbamic acid tert-butyl ester (9A)

At −78° C., to a solution of 7B (400 mg, 1.51 mmol) in 5 mL of THF was added MeLi (1.6 M in ether, 2.36 mL, 3.78 mmol) dropwise. The mixture was stirred at −78° C. for 30 minutes before it was quenched by 5 mL of $NH_4Cl$ aq (Sat'd) solution. The mixture was extracted by DCM (5 mL×3) and the combined DCM layers were dried over $Na_2SO_4$. Solvent was remove under vacuum and the residue was purified by silica gel chromatography [0 to 5% of MeOH in DCM:Hexane 1:1(v/v)] to give the title compounds (9A) as a mixture of equatorial and axial isomers (310 mg, 7.3%)). LC-MS (ESR): m/z=282 (M+H)⁺.

Step 2: (4-Fluoro-4-methyl-adamantan-1-yl)-carbamic acid tert-butyl ester (9B)

At −78° C., to a solution of (diethylamino)sulfur trifluoride (DAST) (0.78 mL, 0.6 mmol) in DCM (2 mL) was added (4-Hydroxy-adamantan-1-ylmethyl)-carbamic acid tert-butyl ester 1B (140 mg, 0.5 mmol) in DCM (1 mL) dropwise. The reaction mixture was stirred at rt for 1 hour before it was quenched by 2 ml of $NH_4Cl$ aq (Sat'd) solution. The mixture was extracted by DCM (5 mL×3) and the combined organic extracts were dried over $Na_2SO_4$. Solvents were remove under vacuum and the residue was purified by silica gel chromatography (0~25% EtOAc in hexane) to give 9B (120 mg, 80%) as a mixture of equatorial and axial isomers (80%). LC-MS (ESR): m/z=284 (M+H)⁺.

Step 3: 4-Fluoro-4-methyl-adamantan-1-ylamine (9)

To 9b (30 mg) in 2 mL of 1,4-dioxane was added HCl (4N in 1,4-dioxane, 1.0 mL). The mixture was stirred at rt for overnight. The solvent was removed under vacuum. The resulting residue was dissolved in 2 mL of water and was washed with EtOAc (5 mL×3). The water was the removed under vacuum to give the title compound as hydrogen chloride salts (9) respectively (23 mg). LC-MS (ESR): m/z=184 (M+H)⁺

Example 10

5-Amino-adamantane-2-thione (10)

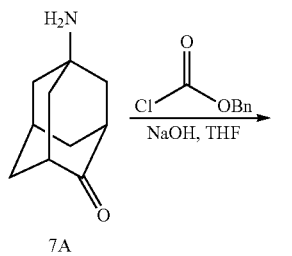

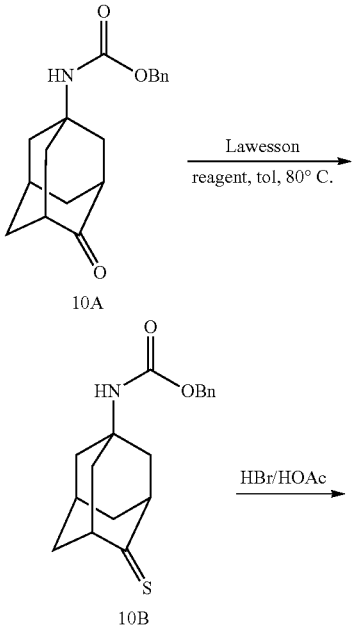

Step 1: (4-Oxo-adamantan-1-yl)-carbamic acid benzyl ester (10A)

Benzyl chloroformate (0.46 mL, 3.31 mmol) was added to a mixture of 7A (500 mg, 3.01 mmol) and K2CO3 (421 mg, 4.5 mmol) in THF (5 mL) at rt and the mixture was stirred over 2 h. The solvent was removed under vacuum and the residue was dissolved in DCM (10 mL) and washed with NaOH (10 mL×3). The organic solution was dried over NaSO$_4$ and solvent was removed under vacuum and the residue was purified by silica gel chromatography [Hexane:EtOAc 4:1(v/v)] to give the title compounds 10A (610 mg, 67%) as a white solid. LC-MS (ESR): m/z=300 (M+H)$^+$.

Step 2: (4-Thioxo-adamantan-1-yl)-carbamic acid benzyl ester (10B)

A mixture of ketone 10A (240 mg, 0.8 mmol) and Lawesson reagent (200 mg, 0.48 mmol) in anhydrous toluene was heated at 70° C. for overnight. The solvent was removed under vacuum and the residue was purified by silica gel chromatography [Hexane:EtOAc 4:1(v/v)] to give the title compounds 10B (130 mg, 54%). LC-MS (ESR): m/z=316 (M+H)$^+$.

Step 3: 5-Amino-adamantane-2-thione (10)

To 10B (30 mg, 0.10 mmol) was added HBr (33% in HOAc) 2 mL and the mixture was stirred at rt for 1 h. Ether (10 mL×2) was added and the resulting precipitate was collected and dried under vacuum to give the title compound as hydrogen bromide salts (10) (20 mg). LC-MS (ESR): m/z=182 (M+H)$^+$

Example 11

5-Amino-adamantane-2-thiol

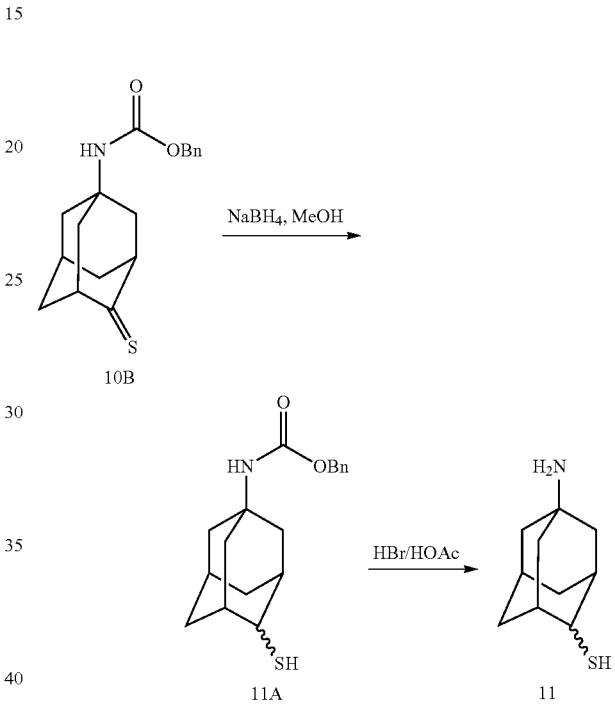

Step 1: (4-Mercapto-adamantan-1-yl)-carbamic acid benzyl ester (11A)

Ketone 10B (100 mg, 0.317 mmol) in 5 ml of absolute MeOH was added NaBH$_4$ (23 mg, 0.62 mmol) in portions at 0° C. The reaction was stirred for 1 h, at which time the solution was carefully quenched with water. The reaction mixture was extracted with EtOAc twice and the organic phases were combined, dried (anhydrous Na$_2$SO$_4$), and concentrated. The crude mixture was purified by column chromatography (0~10% MeOH in EtOAc) to yield 51 mg of the desired mixture of alcohols 11A LC-MS (ESR): m/z=318 (M+H)$^+$.

Step 2: 5-Amino-adamantane-2-thiol (11)

To 11A (51 mg, 0.16 mmol) was added HBr (33% in HOAc) 2 mL and the mixture was stirred at rt for 2 h. Ether (10 mL×2) was added and the resulting precipitate was collected and dried under vacuum to give the title compound as hydrogen bromide salts (11). LC-MS (ESR): m/z=184 (M+H)$^+$

Example 12 and 13

4-Fluoromethyl-adamantan-1-ylamine

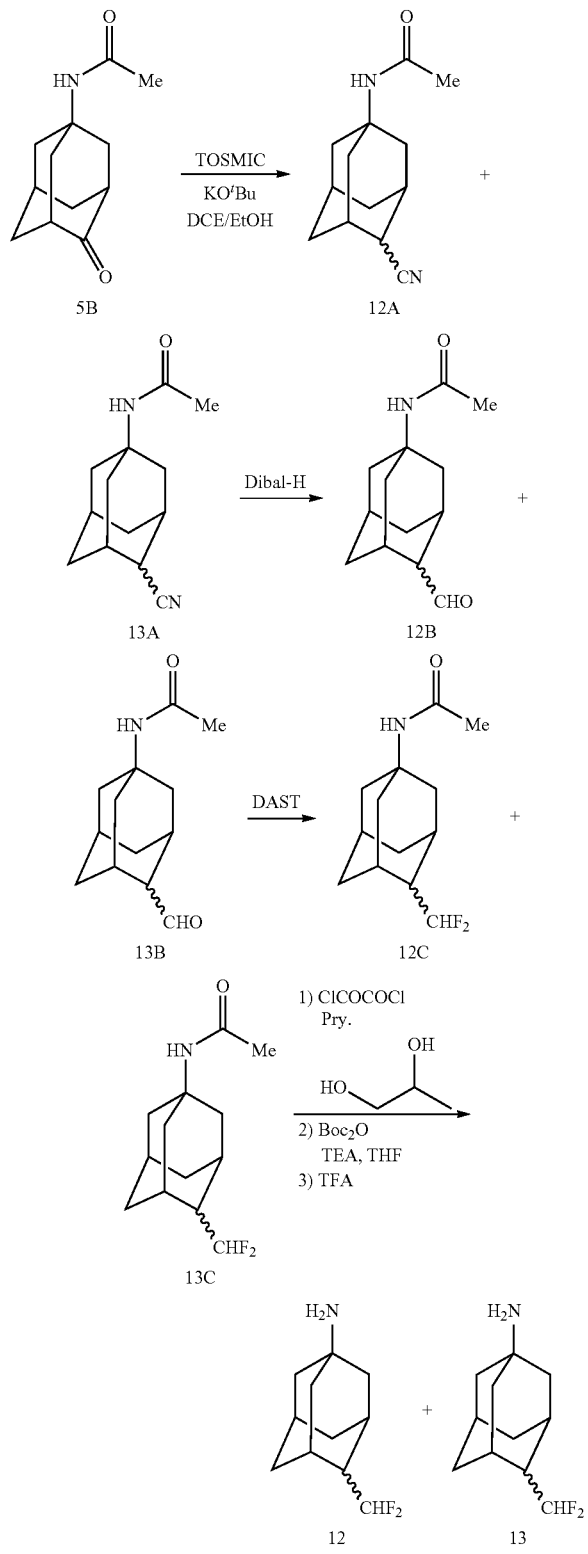

Step 1. Synthesis of nitriles 4-Difluoromethyl-adamantan-1-ylamine (12A and 13A)

Solid t-BuOK (1.6381 g) was added as 8 portions to a solution of ketone 25A (762.1 mg) and TosMIC (1.0123 g) in a mixture of DME (35 mL) and absolute EtOH (0.60 mL) while keeping the temperature between 5 and 10° C. The reaction mixture was allowed to warm to rt and was maintained for 30 min. The reaction mixture was then heated at 35-40° C. for 30 min and was then allowed to cool to rt. The precipitate (TosK) was removed by filtration and the filter cake was washed with DME. The combined organic layers were concentrated and the residue was purified by column chromatography (0/100 to 10/90 MeOH/EtOAc) to provide nitrile 12A (308.1 mg, less polar isomer) and nitrile 13A (343.0 mg, more polar isomer) as separate compounds. Data: LC/MS (ESR): 12A: m/z 219.0 $[M+H]^+$, 241.1 $[M+Na]^+$; 13A: m/z 219.1 $[M+H]^+$, 241.1 $[M+Na]^+$.

Step 2. Synthesis of aldehydes N-(4-Formyl-adamantan-1-yl)-acetamide (12B) and (13B)

A 1.0 M solution of DIBAL-H in hexane (0.75 ml, 0.75 mmol) was added dropwise to a solution of nitrile 12A (48.8 mg) in DCM (4.0 mL) at −78° C. The reaction mixture was allowed to slowly warm to rt and maintained at rt for 3 h. The reaction was carefully quenched with a 1 M aqueous solution of HCl. The reaction mixture was extracted with EtOAc (2×) and the combined organic layers were dried ($Na_2SO_4$), and concentrated. The residue was purified by silica gel chromatography (0/100 to 10/90 MeOH/EtOAc) to provide 24.1 mg of aldehyde 12B. LC/MS (ESR) m/z=222.1 $[M+H]^+$, 244.0 $[M+Na]^+$.

Aldehyde 13B was prepared from nitrile 13B using the reaction conditions that were used to prepare aldehyde 12B. LC/MS (ESR) m/z=236.1 $[M+H]^+$, 244.0 $[M+Na]^+$.

Step 3. Synthesis of difluorides (12C) and (13C)

DAST (0.20 mL) was added dropwise over a period of 10 min to a solution of aldehyde 12B (44.9 mg) in DCM (5 mL) at −78° C. The reaction mixture was maintained at −78° C. for 10 min and then was allowed to slowly warm to rt. After 1 h at rt, the reaction was carefully diluted with water and was extracted with DCM (2×). The combined organic layers were dried ($Na_2SO_4$), and concentrated. The residue was purified by silica gel chromatography (0/100 to 5/95 MeOH/EtOAc) to provide 46.9 mg of difluoromethyl analog 12C. LC/MS (ESR) m/z=244.1 $[M+H]^+$.

Difluoromethyl analog 13C was prepared from aldehyde 13B using the reaction conditions that were used to prepare the difluoromethyl analog 12C. LC/MS (ESR) m/z=244.1 $[M+H]^+$.

Step 4. Synthesis of 4-Fluoromethyl-adamantan-1-ylamine (12) and (13)

A 2.0 M solution of oxalyl chloride in DCM (0.12 mL) was added dropwise to a solution of amide 12C (60.1 mg) in dry THF (5 mL) and pyridine (0.03 mL) at 0° C. The reaction mixture was maintained at 0° C. for 45 min when 1,2-propanediol (0.04 mL) was added in one portion and the reaction was allowed to warm to rt. The reaction mixture was diluted with EtOH (4 mL) and was concentrated. The crude oil was partitioned between 1 M aqueous HCl and TBME (10 mL) and the layers were separated. The organic phase was extracted with 1.0 M aqueous HCl solution (1×) and the pH of the combined aqueous layers was adjusted to pH 11 with 4 N aqueous NaOH. The aqueous layer was then extracted EtOAc (2×) and the combined organic layers were dried (Na₂SO₄), and concentrated to provide the crude amine.

Boc-anhydride (90.1 mg) and TEA (0.5 mL) was added sequentially to a solution of the crude amine in THF (5 mL) and the reaction mixture was maintained at rt for 2 h. The reaction mixture was diluted with NaHCO₃ solution and the aqueous layer was extracted with EtOAc (2×). The combined organic layers were dried (Na₂SO₄) and concentrated. The residue was purified by silica gel chromatography (0/100 to 20/80 EtOAc/hexane) to provide 40.1 mg of the pure carbamate.

The pure carbamate (40.1 mg) was diluted with a solution of 4 N HCl in dioxane (1.5 mL) and the reaction mixture was maintained at rt for 2 h. The reaction mixture was concentrated and the residue was triturated with ether (3×) and dried to provide 23.6 mg of amine 12 as a white solid.

Amine 13 was prepared from amide 13C using the reaction conditions that were used to prepare amine 12.

Example 14

5-Amino-adamantan-2-one oxime

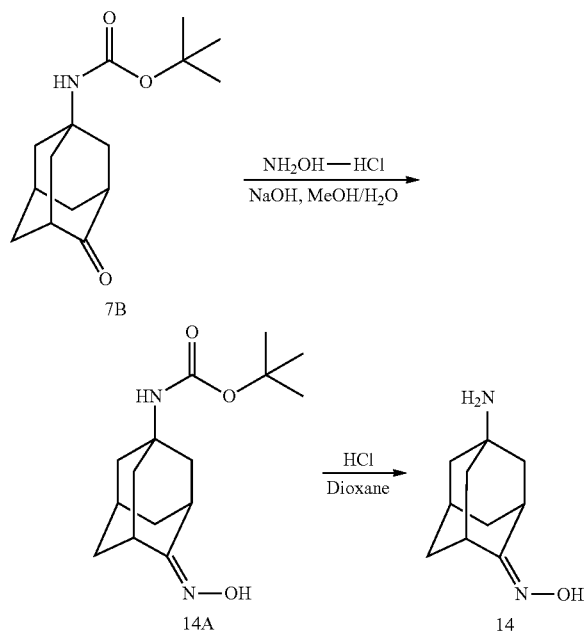

Step 1: (4-Hydroxyimino-adamantan-1-yl)-carbamic acid tert-butyl ester (14A)

The mixture of ketone 7b (1.0 mmol), NH₂OH—HCl (5 mmol), and NaOH (5 mmol) was diluted with EtOH (5 mL) and H₂O (1 mL) and the reaction mixture was heated at 80° C. for 16 h. Upon cooling, the reaction mixture was extracted with DCM (10 mL×3) and the combined organic layers were dried (Na₂SO₄) and concentrated to provide oxime 14A in 90% yield as a solid. The material was used in the next step without further purification. Data: LC/MS (ESR) m/z=295 [M+H]⁺.

Step 2. Synthesis of 5-Amino-adamantan-2-one oxime (14)

A solution of oxime 14A (0.17 mmol) in 1,4-dioxane (2.0 mL) was diluted with a solution of 4 N HCl in dioxane (1.0 mL) and the reaction mixture was maintained at rt for 16 h. The reaction mixture was concentrated and dried to provide amine 14 in 88% yield as a hydrochloric acid salt. Data: LC/MS (ESR) m/z=195 [M+H]⁺.

Example 15

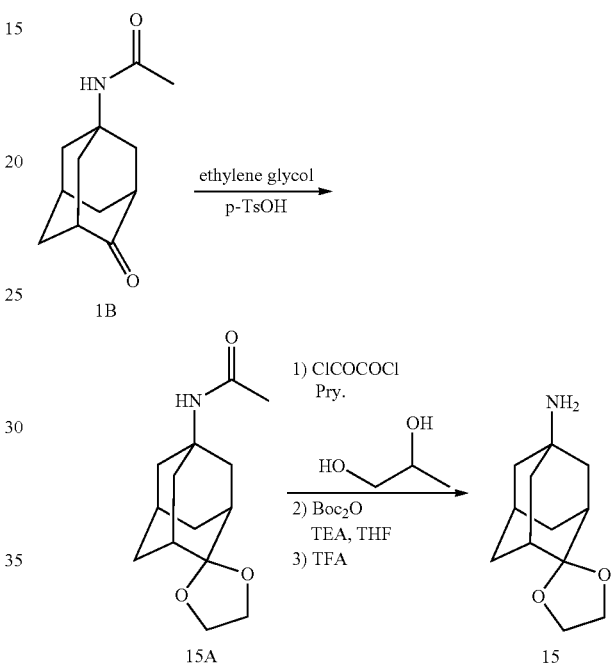

Step 1. Synthesis of (15A)

To a solution of 248.0 mg of the ketone 1B in 10 ml of benzene was added 1.0 ml of ethylene glycol and 36.4 mg of p-TsOH—H₂O sequentially. The resulting mixture was heated to reflux for 2 h when the reaction was quenched by the addition of NaHCO₃ aqueous solution. The reaction mixture was extracted with EtOAc twice and the organic phases were combined, dried (over anhydrous Na₂SO₄), and concentrated. The crude mixture was purified by column chromatography (0~50% EtOAc in DCM) to yield 253.5 mg of 15A. LC/MS (ESR) m/z=252.2 [M+H]⁺.

Step 2. Synthesis of (15)

A 2.0 M solution of oxalyl chloride in DCM (0.25 mL) was added dropwise to a solution of amide 15A (101.2 mg) in dry THF (8 mL) and pyridine (0.05 mL) at 0° C. The reaction mixture was maintained at 0° C. for 45 min when 1,2-propanediol (0.045 mL) was added in one portion and the reaction was allowed to warm to rt. The reaction mixture was diluted with EtOH (5 mL) and was concentrated. The crude oil was partitioned between 1 M aqueous HCl and TBME (10 mL) and the layers were separated. The organic phase was extracted with 1.0 M aqueous HCl solution (1×) and the pH of the combined aqueous layers was adjusted to pH 11 with 4 N aqueous NaOH. The aqueous layer was then extracted EtOAc (2×) and the combined organic layers were dried (Na$_2$SO$_4$), and concentrated to provide the crude amine.

Boc-anhydride (308.6 mg) and TEA (1.0 mL) was added sequentially to a solution of the crude amine in THF (10 mL) and the reaction mixture was maintained at rt for 2 h. The reaction mixture was diluted with NaHCO$_3$ solution and the aqueous layer was extracted with EtOAc (2×). The combined organic layers were dried (Na$_2$SO$_4$) and concentrated. The residue was purified by silica gel chromatography (0/100 to 25/75 EtOAc/hexane) to provide 83.0 mg of the pure carbamate.

The pure carbamate (36.3 mg) in 2.0 ml of DCM was treated with 1.0 ml of TFA at rt and the reaction mixture was maintained at rt for 2 h. The reaction mixture was concentrated and the residue was triturated with ether (3×) and dried to provide 28.2 mg of amine 15 as an off white solid.

Example 16

C-(4-Methoxy-adamantan-1-yl)-methylamine

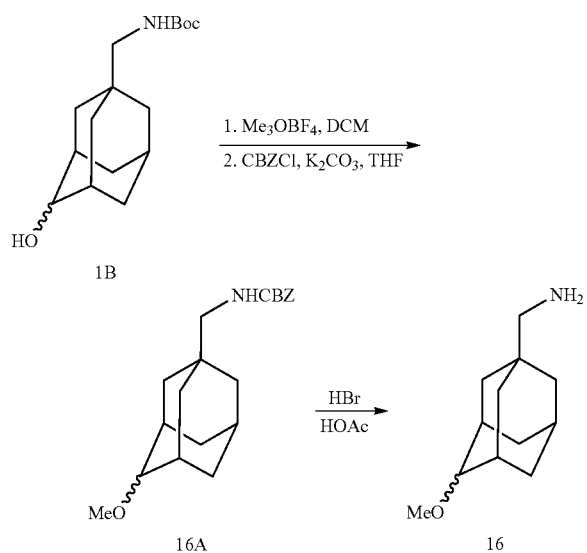

Step 1:
(4-Methoxy-adamantan-1-ylmethyl)-carbamic acid tert-butyl ester (16A)

At rt, Me$_3$OBF$_4$ (200 mg, 1.5 mmol) was added to a solution of alcohol 1B (280 mg, 1 mmol) in DCM (5 mL). After the mixture was stirred for 3 h, it was quenched with H$_2$O (1 mL). The mixture was extracted by DCM (10 mL×3) and the combined DCM layers were dried over Na$_2$SO$_4$. Solvent was removed under vacuum and the residue was used without further purification.

Benzyl chloroformate (0.23 mL, 1.66 mmol) was added to above residue and K$_2$CO$_3$ (210 mg, 2.2 mmol) in THF (3 mL) at rt and the mixture was stirred over 2 h. The solvent was removed under vacuum and the residue was dissolved in DCM (10 mL) and washed with NaOH (10 mL×3). The organic solution was dried over NaSO$_4$ and solvent was removed under vacuum and the residue was purified by silica gel chromatography [Hexane:EtOAc 2:1(v/v)] to give the title compounds 16A (231 mg, 70%). LC-MS (ESR): m/z=330 (M+H)$^+$.

Step 2: C-(4-Methoxy-adamantan-1-yl)-methylamine (16)

To 16A (30 mg, 0.10 mmol) in was added HBr (30% in HOAc) 1 mL and the mixture was stirred at rt for 2 h. Ether (10 mL×2) was added and the resulting precipitate was collected and dried under vacuum to give the title compound as hydrogen bromide salts (16). LC-MS (ESR): m/z=196 [M+H]$^+$.

Example 17

5-Aminomethyl-adamantane-2-carbonitrile

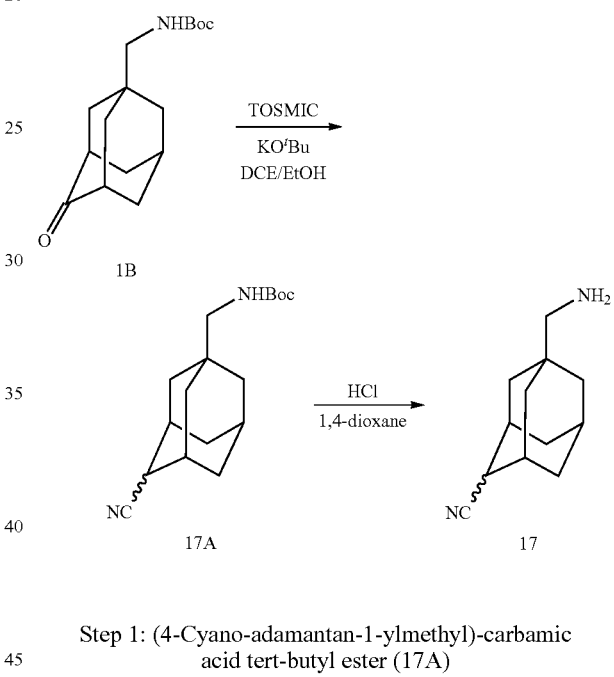

Step 1: (4-Cyano-adamantan-1-ylmethyl)-carbamic acid tert-butyl ester (17A)

Solid t-BuOK (240 mg, 2.15 mmol) was added as 6 portions to a solution of ketone 1B (300 mg, 1.07 mmol) and TosMIC (273 mg, 1.40 mmol) in a mixture of DME (5.0 mL) and absolute EtOH (1 mL) while keeping the temperature between 5 and 10° C. The reaction mixture was allowed to warm to rt and was maintained for 30 min. The reaction mixture was then heated at 35-40° C. for 30 min and was then allowed to cool to rt. The precipitate (TosK) was removed by filtration and the filter cake was washed with DME. The combined organic layers were concentrated and the residue was purified by column chromatography (0/100 to 10/90 MeOH/EtOAc) to provide nitrile 17A (203 mg, 70%) as a mixture of equatorial and axial isomers. Data: LC/MS (ESR) m/z=291 [M+H]$^+$.

Step 2: 5-Aminomethyl-adamantane-2-carbonitrile (17)

A solution of 16A (30 mg, 0.13 mmol) in 1,4-dioxane (2.0 mL) was diluted with a solution of 4 N HCl in dioxane (1.0 mL) and the reaction mixture was maintained at rt for 16 h.

The reaction mixture was concentrated and dried to provide amine 17 (21 mg) as a hydrochloric acid salt. Data: LC/MS (ESR) m/z=191 [M+H]⁺.

Example 18

5-Nitromethyl-adamantan-2-ol (18)

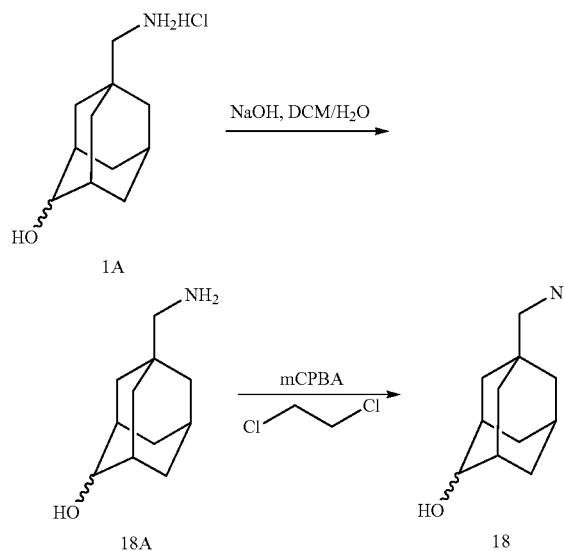

5-Aminomethyl-adamantan-2-ol hydrogen chloride salt 1A (1.0 g, 4.6 mmol) was added to NaOH (1N, 10 mL) and extracted with DCM (5 mL×3). The organic layer was dried over Na₂SO₄. Solvent was removed under vacuum to give free base 18A (700 mg). A mixture of 17A (360 mg, 18 mmol) and mCPBA (1.3 g, 70% pure, 54 mmol) in DCE (20 mL) was heated at 80° C. for 2 h and cooled to rt. The mixture was diluted with DCM (10 mL) and washed with saturated Na2S2O3 and Na2CO3 (3×10 ml). The organic layer was dried over Na₂SO₄. Solvent was remove under vacuum to give pure nitro 18 as a white solid (300 mg, 84%). ¹H NMR (300 MHz, CDCl₃) δ 3.85 (m, 1H), 3.74 (s, 2H), and 2.2-1.5 (13H, m).

Example 19

4-Fluoro-1-nitromethyl-adamantane

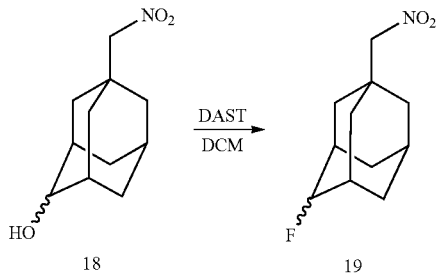

At −78° C., to a solution of 18 (100 mg, 0.47 mmol) in DCM (5 mL) was added (diethylamino)sulfur trifluoride (DAST) (0.78 mL, 0.6 mmol). The reaction mixture was stirred at rt for 1 hour before it was quenched by 1 ml of H₂O. The mixture was extracted by DCM (5 mL×3) and the combined organic extracts were dried over Na₂SO₄. Solvents were remove under vacuum and the residue was purified by silica gel chromatography (0 to 5% of MeOH in DCM:Hexane 1:1(v/v)) to give 19 (70 mg, 70%). LC-MS (ESR): m/z=213 (M)⁺. ¹H NMR (300 MHz, CDCl₃) δ 4.70 (dd, J=4.3, 4.7, 0.5H), 4.50 (dd, J=4.3, 4.7, 0.5H), 4.1 (s, 2H), 2.2-1.5 (13H, m).

Example 20

1-Amino-2-methyl-adamantan-2-ol

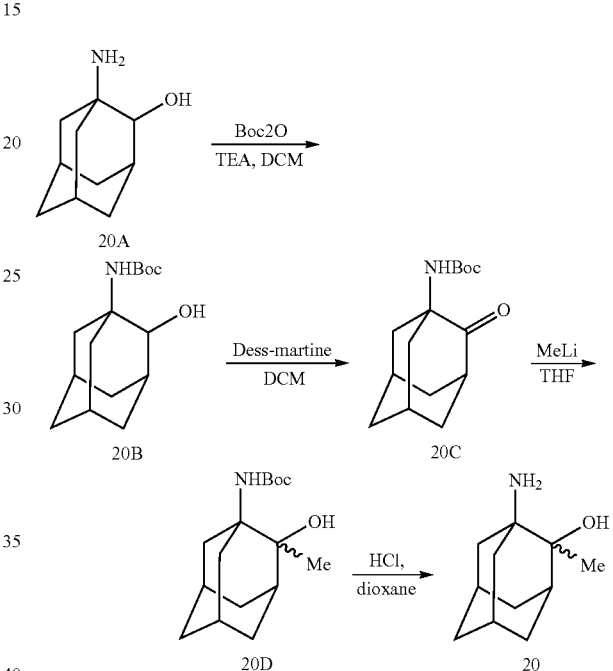

Step 1: (2-Hydroxy-adamantan-1-yl)-carbamic acid tert-butyl ester (20B)

At 0° C., to a solution of 1-Amino-adamantan-2-ol 20A (700 mg, 4.2 mmol) in dichloromethane (DCM, 10 mL) were added triethylamine (TEA, 1 mL). Boc₂O (1.1 g, 5 mmol) in DCM (10 mL) was added to above solution slowly. The resulting solution was stirred at room temperature (rt) for 10 hours before it was quenched by 10 ml of NH₄Cl aq (Sat'd) solution. The mixture was extracted by DCM (20 mL×3) and the combined DCM layers were dried over Na₂SO₄. Solvent was remove under vacuum gave the title compound 20B as a solid (1.01 g, 90%), which as used to next step without further purification. LC-MS (ESR): m/z=268 (M+H)⁺.

Step 2: (2-Oxo-adamantan-1-yl)-carbamic acid tert-butyl ester (20C)

To a solution of 20B (500 mg, 1.87 mmol) in 10 mL of DCM was added Dess martin periodinane (1.03 g, 3 mmol) at one portion at rt. The mixture was stirred at rt overnight and was quenched by 20 mL of NH₄Cl aq (Sat'd) solution. The mixture was extracted by DCM (5 mL×3) and the combined DCM layers were dried over Na₂SO₄. Solvent was remove under vacuum and the residue was purified by silica gel chromatography (Hexane:EtOAc 2:1(v/v)) to give the title compounds (20C) (510 mg, 90%). LC-MS (ESR): m/z=266 (M+H)+.

Step 3. (2-Hydroxy-2-methyl-adamantan-1-yl)-carbamic acid tert-butyl ester (20D)

At −78° C., to a solution of ketone 20C (500 mg, 1.9 mmol) in 20 mL of THF was added MeLi (1.6 M in ether, 5 mL, 8.0 mmol) dropwise. The mixture was stirred at −78° C. for 30 minutes before it was quenched by 5 mL of NH$_4$Cl aq (Sat'd) solution. The mixture was extracted by DCM (5 mL×3) and the combined DCM layers were dried over Na$_2$SO$_4$. Solvent was remove under vacuum and the residue was purified by silica gel chromatography Hexane:EtOAc 1:1(v/v)) to give the title compounds 20D (410 mg, 77%) as a mixture of equatorial and axial isomers. LC-MS (ESR): m/z=282 (M+H)+.

Step 3. 5-Aminomethyl-2-methyl-adamantan-2-ol (20)

To each of 19D (40 mg, 0.14 mmol) in 2 mL of 1,4-dioxane was added HCl (4N in 1,4-dioxane, 1.0 mL). The mixture was stirred at rt for overnight. The solvent was removed under vacuum. The resulting residue was dissolved in 2 mL of water and was washed with EtOAc (5 mL×3). The water was the removed under vacuum to give the title compound 20 (39 mg, 90%) as hydrogen chloride salt. LC-MS (ESR): m/z=182 (M+H)+.

Example 21

3-Fluoro-1-nitro-adamantane

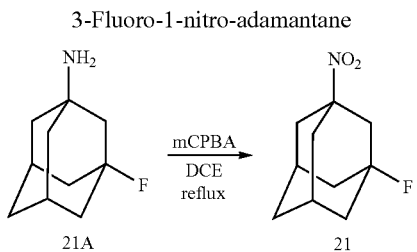

To an 86.2 mg of amine 21A in 3.0 ml of DCE was added 432.7 mg of mCPBA (up to 78% pure) and the reaction mixture was heated to reflux for 6 h. The reaction mixture was diluted with DCM and washed sequentially with saturated NaHCO$_3$ solution, NaHSO$_3$ solution, and saturated NaHCO$_3$ solution. The organic phase was dried (over anhydrous Na$_2$SO$_4$), and concentrated. The crude mixture was purified by column chromatography (0~30% EtOAc in hexane) to yield 30.6 mg of desired product 21 as an LC-MS (ESR): m/z=181.2 (M+H)+.

Example 22

N-(3-Fluoro-adamantan-1-yl)-guanidine

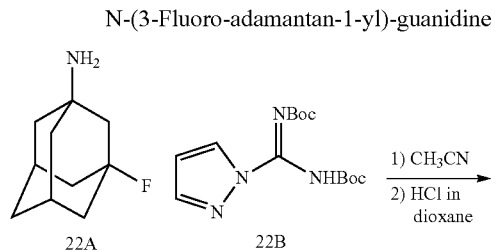

-continued

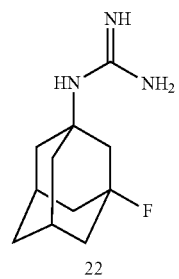

To a 54.1 mg of the amines 22A-HOAc salt in 3.0 ml of CH$_3$CN was sequentially added 0.3 ml of TEA and 266.4 mg of 22B in one portion. The resulting mixture was stirred for overnight. The reaction was quenched with water followed by extraction of EtOAc twice and the organic phases were combined, dried (over anhydrous Na$_2$SO$_4$), and concentrated. The crude residue was purified by column chromatography (0~12% EtOAc in hexane) to yield 22.3 mg of the Boc-protected 22. LC-MS (ESR): m/z=412.3 (M+H)+.

A solution of HCl/dioxane (2 ml, 4.0 M) was added to the Boc-protected 22 (19.9 mg) in one portion with stirring. After 4 h, LC-MS indicated that the reaction was completed. The reaction mixture was concentrated by rotary evaporation under high vacuum at rt. The residue was then washed with dry ether three times. The white solid yielded (22) was under high vacuum for overnight. Yield is 12.3 mg. LC-MS (ESR): m/z=212.2 (M+H)+.

Example 23

Cell-Free Electrophysiology of M2 Proton Channels

The drug sensitivity of A/M2 proteins (wild type or S31N mutant) was measured using cell-free electrophysiology on solid supported membranes (SSM) (Schulz et al., Methods, 2008, 46, 97-103). For the SSM-based measurements cell membranes expressing the target protein are adsorbed to an SSM-coated gold sensor and the protein activity is evoked by substrate, or ligand concentration jumps, as appropriate. The resulting protein-dependent charge translocation is measured as a transient electrical current.

SSM-Based Biosensors and Measurements

The biosensors were prepared with single-gold-electrode sensors from IonGate Biosciences (Germany) as described by the manufacturer. Briefly, the SSM was built on the gold electrode by applying first an alkane-thiol monolayer followed by a phospholipid monolayer on top of it. Subsequently, the SSM-coated sensors were covered with 100 μl of the ice cold M2 sensor preparation buffer (30 mM MES/KOH, pH 5.8, 140 KCl, 4 mM MgCl$_2$, 0.2 mM DTT) and incubated at 4° C. for 15 minutes. An aliquot of CHO membranes expressing M2 protein was rapidly thawed, diluted with the sensor preparation buffer to a final protein concentration of 0.5-1 μg/μL, and sonicated with a microsonicator by applying 5 bursts with an amplitude of 30% (ultrasonic processor UP 50 H with a MS 1 tip, Dr. Hielscher, Germany). 5-10 μg total protein of the sonicated membranes were loaded per each sensor, centrifuged for 30 minutes at 3,000 rpm and 4° C., and incubated for 24 hours at 4° C. The membrane-loaded biosensors were integrated into the fluidic system of the SURFE$^2$R device (Surface Electrogenic Event Reader, IonGate Biosciences, Germany) and the A/M2 was activated through pH jumps by exchanging a "non-activating" solution (30 mM MOPS/KOH, pH 7.0, 140 KCl, 4 mM MgCl$_2$) for an "activating" solution (30 mM MES/KOH, pH 6.0, 140 KCl, 4 mM MgCl$_2$). For the inhibition experiments, the compounds to be tested as inhibitors were supplied at the same concentration to both solutions. Responses in the presence of the compounds of Formula (I) were normalized to the currents evoked by the application of the activating (pH 6.0) solution without inhibitor (Io) and are calculated as % inhibition=100×(1−I/Io).

Representative compounds of Formula (I) were tested using the above protocol with results summarized in Table 1. The resulting inhibition is indicated as falling into one of three ranges: 51-95% (A), 11-50% (B), and 1-10% (C).

TABLE 1

| Cpd # | Structure | IonGate_M2(S31)_ Screen % Inhibition at 25 μM | Reference |
|---|---|---|---|
| 1 | 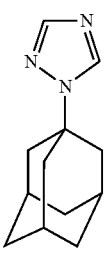 [SMILES: c1ncn(C23CC4CC(CC(C4)C2)C3)n1] | B | CAS: 69625-62-3 |
| 2 | 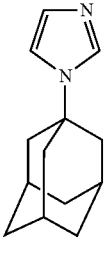 [SMILES: c1cn(C23CC4CC(CC(C4)C2)C3)cn1] | B | CAS: 69380-11-6 |
| 3 | 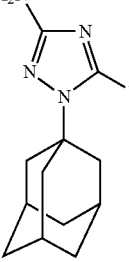 | B | CAS: 415686-37-2 |
| 4 | 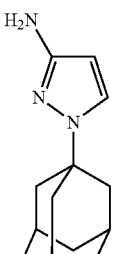 | B | CAS: 128315-61-7 |

TABLE 1-continued

| Cpd # | Structure | IonGate_M2(S31)_ Screen % Inhibition at 25 μM | Reference |
|---|---|---|---|
| 5 | 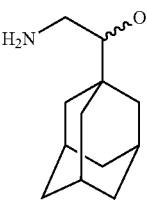 | A | Racemic, CAS: 76066-33-6 |
| 6 | 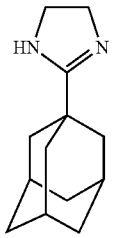 | A | CAS: 906811-70-9 |
| 7 | 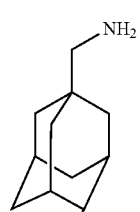 | B | A mixture of stereoisomers, CAS: 1053170-70-9 |
| 8 | 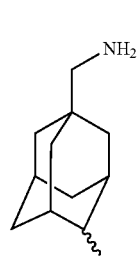 | A | Example 1 One of two stereoisomers |
| 9 | 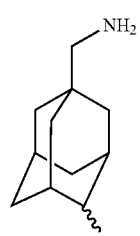 | A | Example 2 One of two stereoisomers |
| 11 | 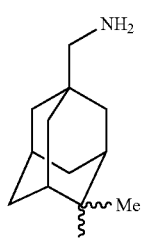 | B | Example 3 One of two stereoisomers |

TABLE 1-continued

| Cpd # | Structure | IonGate_M2(S31)_ Screen % Inhibition at 25 μM | Reference |
|---|---|---|---|
| 12 | 1-amino-3-fluoroadamantane (NH₂, F) | A | CAS: 120350-83-6 |
| 13 | amino-adamantane with F substituent | A | Example 5 One of two stereoisomers |
| 14 | amino-adamantane with OH | B | CAS: 22591-69-1 |
| 15 | amino-adamantane with =O (ketone) | B | CAS: 115009-23-9 |
| 16 | amino-adamantane with CN | A | Example 7 A mixture of stereoisomers |
| 17 | amino-adamantane with gem-diF | B | Example 8 |
| 18 | amino-adamantane with Me and F | A | Example 9 A mixture of stereoisomers |
| 19 | amino-adamantane with =S | B | Example 10 |
| 20 | amino-adamantane with SH | B | Example 11 A mixture of stereoisomers, |
| 21 | amino-adamantane with CH₂F | A | Example 12 One of two stereoisomers |
| 22 | amino-adamantane with CH₂F | A | Example 13 One of two stereoisomers |
| 23 | amino-adamantane with =N-OH | B | Example 14 |
| 24 | amino-adamantane with dioxolane spiro | B | Example 15 |

TABLE 1-continued

| Cpd # | Structure | IonGate_M2(S31)_ Screen % Inhibition at 25 μM | Reference |
|---|---|---|---|
| 25 | H2N—[adamantyl]—OMe | A | Example 16 |
| 26 | H2N—[adamantyl]—CN | A | Example 17 |
| 27 | O2N—[adamantyl]—OH | B | Example 18 |
| 28 | O2N—[adamantyl]—F | B | Example 19 |
| 29 | NH2—[adamantyl]—SH | A | CAS: 1049744-72-0 |
| 30 | NO2—[adamantyl]—F | C | Example 21 |
| 31 | H2N—C(=NH)—NH—[adamantyl]—F | B | Example 22 |
| 32 | NH2—[adamantyl]—OMe | C | CAS: 426844-65-7 |
| 34 | NH2—[adamantyl]—OH | A | A mixture of stereoisomers, CAS: 73228-20-3 |
| 35 | NH2—[adamantyl]—OH, Me | B | Example 20 A mixture of stereoisomers |

[1]Activity range: 51-95% (A), 11-50% (B), and 1-10% (C)

In view of the preceding disclosure, it will be understood to those of ordinary skill in the art that the same can be performed within a wide and equivalent range of conditions, formulations, and other parameters without affecting the scope of the invention or any embodiment thereof.

What is claimed is:

1. A method for treating an influenza virus-affected disease state or infection comprising the step of administering to a subject in need thereof a composition comprising a compound of formula I:

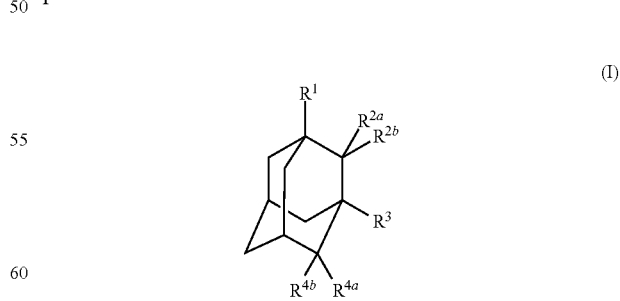

or a pharmaceutically acceptable salt thereof, wherein
$R^1$ is amino, amino($C_1$-$C_3$)alkyl, nitro, nitro($C_1$-$C_3$)alkyl, formamidinyl, guanidinyl, —CH(OH)CH$_2$NO$_2$, ($C_1$-$C_3$)alkylamino, or a five- or six-membered heterocyclic ring;

$R^{2a}$ and $R^{2b}$ are independently hydrogen, hydroxyl, $(C_1-C_3)$alkyl optionally substituted with halo, $(C_1-C_3)$alkoxy, or halo;

or, $R^1$ together with $R^{2a}$ or $R^{2b}$ forms a five- or six-membered optionally substituted carbocyclic or heterocyclic ring;

$R^3$ is hydrogen, halo, hydroxyl, $(C_1-C_3)$alkoxy, thiol, or thio$(C_1-C_3)$alkyl; and, $R^{4a}$ and $R^{4b}$ are independently hydrogen, hydroxyl, halo, thiol, thionyl, cyano, $(C_1-C_3)$alkyl optionally substituted with halo, $(C_1-C_3)$alkoxy, oxo, oxime, hydroxy $(C_1-C_3)$alkyl, or $R^{4a}$ and $R^{4b}$ together with the carbon atom to which they are both attached form a three- to six-membered carbocyclic or heterocyclic ring, wherein:

at least one of $R^{2a}$ or $R^{2b}$; $R^3$; or $R^{4a}$ and $R^{4b}$ are other than hydrogen, or, $R^1$ includes or is involved in forming a five- or six-membered heterocyclic or carbocyclic ring that is directly bound to the carbon atom to which $R^1$ is attached wherein the compound is not 3-fluoroadamantan-1-amine.

2. The method according to claim 1 wherein $R^1$ is a substituted or unsubstituted imidazole, pyrazole, or triazole ring.

3. The method according to claim 2 wherein $R^{2a}$, $R^{2b}$, $R^3$, $R^{4a}$, and $R^{4b}$ are hydrogen.

4. The method according to claim 1 wherein $R^1$ is amino $(C_1-C_3)$alkyl.

5. The method according to claim 4 wherein $R^{4a}$ and $R^{4b}$ are independently hydrogen, halo, hydroxyl, $(C_1-C_3)$alkyl, or $(C_1-C_3)$alkoxy.

6. The method according to claim 1 wherein $R^1$ is amino.

7. The method according to claim 4 wherein $R^{4a}$ and $R^{4b}$ are independently hydrogen, halo, hydroxyl, oxo, cyano, $(C_1-C_3)$alkyl optionally substituted with halo, thionyl, thiol, oxime, or $R^{4a}$ and $R^{4b}$ together with the carbon atom to which they are both attached form a three- to six-membered carbocyclic or heterocyclic ring.

8. The method according to claim 7 wherein $R^{2a}$, $R^{2b}$, and $R^3$ are hydrogen.

9. The method according to claim 1 wherein $R^1$ is nitro or nitro$(C_1-C_3)$alkyl.

10. The method according to claim 9 wherein $R^{4a}$ and $R^{4b}$ are independently $(C_1-C_3)$alkoxy, hydroxyl, or halo.

11. The method according to claim 1 wherein $R^1$ together with $R^{2a}$ or $R^{2b}$ forms a five- or six-membered optionally substituted carbocyclic or heterocyclic ring.

12. The method according to claim 1 wherein said virus is an influenza wildtype virus.

13. The method according to claim 1 wherein said influenza virus is a mutant.

14. The method according to claim 1 wherein said compound is:

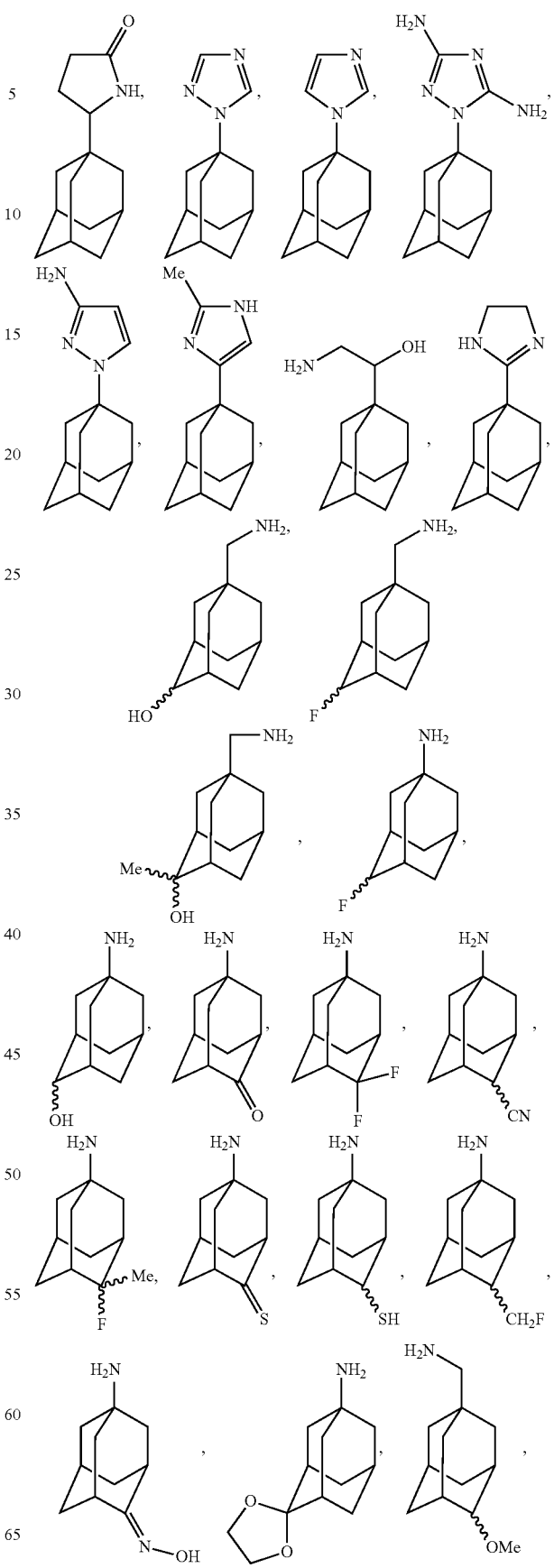

-continued

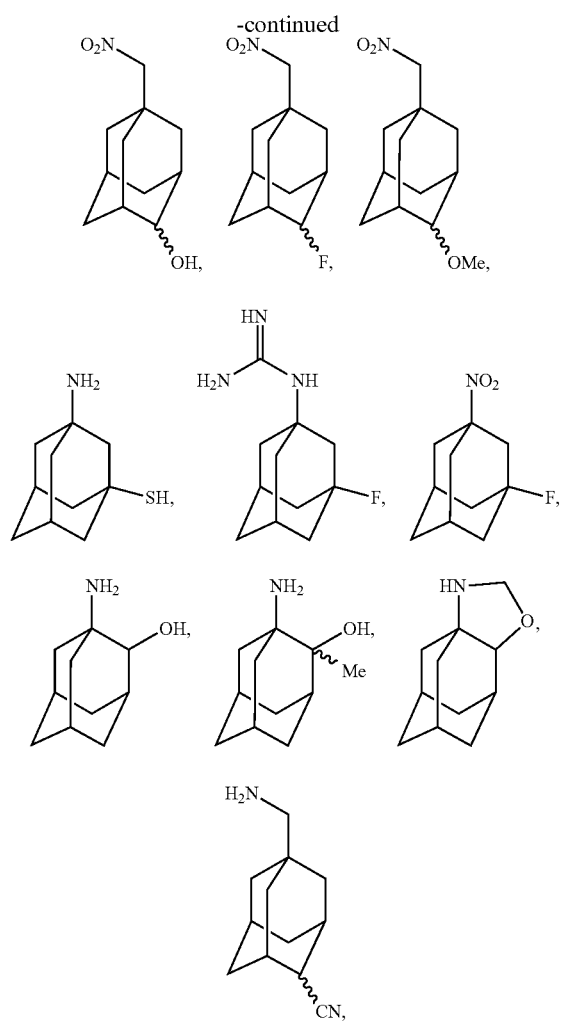

or a pharmaceutically acceptable salt or stereoisomer thereof.

15. A compound according to formula II:

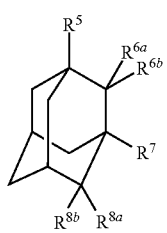

(II)

or a pharmaceutically acceptable salt thereof, wherein (a)
$R^5$ is guanidinyl;
$R^{6a}$ and $R^{6b}$ are independently hydrogen, hydroxyl, or $(C_1\text{-}C_3)$alkyl optionally substituted with halo;
or, $R^5$ together with $R^{6a}$ or $R^{6b}$ forms a five- or six-membered optionally substituted carbocyclic or heterocyclic ring;
$R^7$ is hydrogen or halo; and,
$R^{8a}$ and $R^{8b}$ are independently hydrogen, hydroxyl, halo, cyano, $(C_1\text{-}C_3)$alkyl optionally substituted with halo, $(C_1\text{-}C_3)$alkoxy, thiol, thionyl, oxime, or $R^{8a}$ and $R^{8b}$ together with the carbon atom to which they are both attached form a three- to six-membered carbocyclic ring, or, (b)
$R^5$ is amino;
$R^{6a}$ and $R^{6b}$ are independently hydrogen, hydroxyl, or $(C_1\text{-}C_3)$alkyl optionally substituted with halo;
or, $R^5$ together with $R^{6a}$ or $R^{6b}$ forms a five- or six-membered optionally substituted carbocyclic or heterocyclic ring;
$R^7$ is hydrogen or halo; and,
$R^{8a}$ is hydroxyl, halo, cyano, $(C_1\text{-}C_3)$alkyl optionally substituted with halo, $(C_1\text{-}C_3)$alkoxy, thiol, thionyl, or oxime;
$R^{8b}$ is hydroxyl, cyano, $(C_1\text{-}C_3)$alkyl optionally with halo, $(C_1\text{-}C_3)$alkoxy, thiol, thionyl, or oxime;
or, $R^{8a}$ and $R^{8b}$ together with the carbon atom to which they are both attached form a three- to six-membered carbocyclic ring, or, (c)
$R^5$ is amino$(C_1\text{-}C_3)$alkyl, nitro$(C_1\text{-}C_3)$alkyl, or guanidinyl;
$R^{6a}$ and $R^{6b}$ are independently hydrogen, hydroxyl, or $(C_1\text{-}C_3)$alkyl optionally substituted with halo;
or, $R^5$ together with $R^{6a}$ or $R^{6b}$ forms a five- or six-membered optionally substituted carbocyclic or heterocyclic ring;
$R^7$ is hydrogen or halo;
$R^{8a}$ is hydrogen or $R^{8a}$ and $R^{8b}$ together with the carbon atom to which they are both attached form a three- to six-membered carbocyclic ring; and,
$R^{8b}$ is hydroxyl, cyano, $(C_1\text{-}C_3)$alkyl optionally substituted with halo, $(C_1\text{-}C_3)$alkoxy, thiol, thionyl, oxime, or $R^{8a}$ and $R^{8b}$ together with the carbon atom to which they are both attached form a three- to six-membered carbocyclic ring;

or, (d)
$R^5$ is amino$(C_1\text{-}C_3)$alkyl or guanidinyl;
$R^{6a}$ and $R^{6b}$ are independently hydrogen, hydroxyl, or $(C_1\text{-}C_3)$alkyl optionally substituted with halo;
or, $R^5$ together with $R^{6a}$ or $R^{6b}$ forms a five- or six-membered optionally substituted carbocyclic or heterocyclic ring;
$R^7$ is hydrogen; and,
$R^{8a}$ and $R^{8b}$ are independently hydrogen, hydroxyl, halo, cyano, $(C_1\text{-}C_3)$alkyl optionally substituted with halo, $(C_1\text{-}C_3)$alkoxy, thiol, thionyl, oxime, or $R^{8a}$ and $R^{8b}$ together with the carbon atom to which they are both attached form a three- to six-membered carbocyclic ring, or, (e)
$R^5$ is amino$(C_1\text{-}C_3)$alkyl or guanidinyl;
$R^{6a}$ and $R^{6b}$ are independently hydrogen, hydroxyl, or $(C_1\text{-}C_3)$alkyl optionally substituted with halo;
or, $R^5$ together with $R^{6a}$ or $R^{6b}$ forms a five- or six-membered optionally substituted carbocyclic or heterocyclic ring;
$R^7$ is hydrogen or halo; and,
$R^{8a}$ is hydrogen, hydroxyl, halo, cyano, $(C_1\text{-}C_3)$alkyl optionally substituted with halo, $(C_1\text{-}C_3)$alkoxy, thiol, thionyl, oxime;

$R^{8b}$ is hydroxyl, halo, cyano, ($C_1$-$C_3$)alkyl optionally substituted with halo, ($C_1$-$C_3$)alkoxy, thiol, thionyl, oxime;

or, $R^{8a}$ and $R^{8b}$ together with the carbon atom to which they are both attached form a three- to six-membered carbocyclic ring, or, (f)
$R^5$ is nitro($C_1$-$C_3$)alkyl;
$R^{6a}$ and $R^{6b}$ are independently hydrogen, hydroxyl, or ($C_1$-$C_3$)alkyl optionally substituted with halo;
or, $R^5$ together with $R^{6a}$ or $R^{6b}$ forms a five- or six-membered optionally substituted carbocyclic or heterocyclic ring;
$R^7$ is hydrogen or halo; and,
$R^{8a}$ and $R^{8b}$ are independently hydrogen, hydroxyl, cyano, ($C_1$-$C_3$)alkyl optionally substituted with halo, ($C_1$-$C_3$)alkoxy, thiol, thionyl, or oxime; or $R^{8a}$ and $R^{8b}$ are both halo; or $R^{8a}$ and $R^{8b}$ together with the carbon atom to which they are both attached form a three- to six-membered carbocyclic ring, or, (g)
$R^5$ is amino;
$R^{6a}$ and $R^{6b}$ are independently hydrogen, hydroxyl, or ($C_1$-$C_3$)alkyl optionally substituted with halo;
or, $R^5$ together with $R^{6a}$ or $R^{6b}$ forms a five- or six-membered optionally substituted carbocyclic or heterocyclic ring;
$R^7$ is hydrogen or halo;
$R^{8a}$ is hydrogen or $R^{8a}$ and $R^{8b}$ together with the carbon atom to which they are both attached form a three- to six-membered carbocyclic ring; and,
$R^{8b}$ is hydroxyl, cyano, ($C_1$-$C_3$)alkyl optionally substituted with halo, thiol, thionyl, oxime, or $R^{8a}$ and $R^{8b}$ together with the carbon atom to which they are both attached form a three- to six-membered carbocyclic ring;
wherein said compound is substituted at two or more positions, and
wherein if $R^5$ includes an —$NH_2$ group, and one of $R^{6a}$ and $R^{6b}$, or one of $R^{8a}$ and $R^{8b}$ is hydroxyl, then the other of $R^{6a}$ and $R^{6b}$ or the other of $R^{8a}$ and $R^{8b}$ are not hydrogen.

16. The compound according to claim 15 wherein $R^5$ is amino($C_1$-$C_3$)alkyl.

17. The compound according to claim 16 wherein $R^{8a}$ and $R^{8b}$ are independently hydrogen, halo, hydroxyl, ($C_1$-$C_3$)alkyl, or ($C_1$-$C_3$)alkoxy.

18. The compound according to claim 15 wherein $R^5$ is amino.

19. The compound according to claim 18 wherein $R^{8a}$ and $R^{8b}$ are independently halo, hydroxyl, cyano, ($C_1$-$C_3$)alkyl optionally substituted with halo, thionyl, thiol, oxime, or $R^{8a}$ and $R^{8b}$ together with the carbon atom to which they are both attached form a three- to six-membered carbocyclic ring.

20. The compound according to claim 18 wherein $R^{6a}$, $R^{6b}$, and $R^7$ are hydrogen.

21. The compound according to claim 15 wherein $R^5$ is nitro($C_1$-$C_3$)alkyl.

22. The compound according to claim 21 wherein $R^{8a}$ and $R^{8b}$ are independently ($C_1$-$C_3$)alkoxy, hydroxyl, or halo.

23. The compound according to claim 15 wherein $R^5$ together with $R^{6a}$ or $R^{6b}$ forms a five- or six-membered optionally substituted carbocyclic or heterocyclic ring.

24. The compound according to claim 15 wherein said compound is:

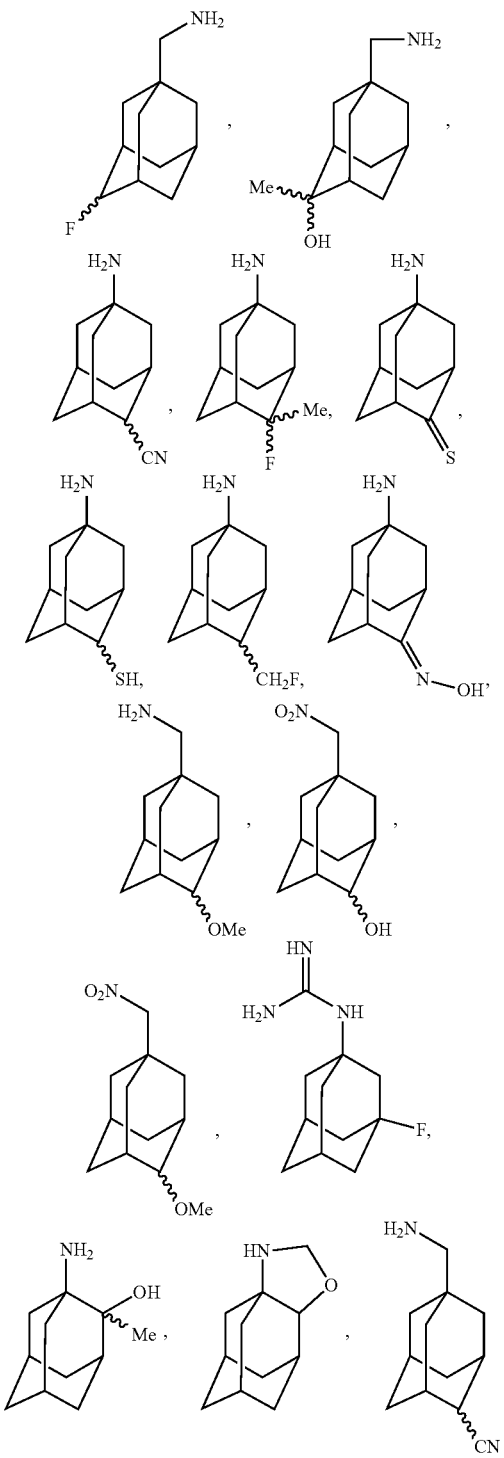

or a pharmaceutically acceptable salt or stereoisomer thereof.

25. A composition comprising a compound according to claim 15 or a pharmaceutically acceptable salt or stereoisomer thereof and a pharmaceutically acceptable carrier, diluent, or excipient.

26. The composition according to claim 25 further comprising a therapeutically effective amount of a further agent that modulates an influenza virus.

* * * * *